(12) United States Patent
De Ley et al.

(10) Patent No.: US 10,772,333 B2
(45) Date of Patent: Sep. 15, 2020

(54) MOLLUSK-KILLING BIOPESTICIDE

(71) Applicant: The Regents of the University of California, Oakland, CA (US)

(72) Inventors: Irma Tandingan De Ley, Riverside, CA (US); Rory McDonnell, Temecula, CA (US); Timothy Paine, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/765,456

(22) PCT Filed: Sep. 30, 2016

(86) PCT No.: PCT/US2016/054969
§ 371 (c)(1),
(2) Date: Apr. 2, 2018

(87) PCT Pub. No.: WO2017/059342
PCT Pub. Date: Apr. 6, 2017

(65) Prior Publication Data
US 2018/0289012 A1 Oct. 11, 2018

Related U.S. Application Data

(60) Provisional application No. 62/236,674, filed on Oct. 2, 2015.

(51) Int. Cl.
*A01N 63/00* (2020.01)
*A01K 67/033* (2006.01)
(Continued)

(52) U.S. Cl.
CPC ............ *A01N 63/00* (2013.01); *A01K 67/033* (2013.01); *A61K 39/07* (2013.01); *A01N 25/008* (2013.01)

(58) Field of Classification Search
None
See application file for complete search history.

(56) References Cited

U.S. PATENT DOCUMENTS 5,527,525 A 6/1996 Wilson et al.
5,849,284 A * 12/1998 Wilson ................... A01N 63/00
424/93.1

FOREIGN PATENT DOCUMENTS

EP 2389805 A2 11/2011
GB 2463501 A 3/2010
(Continued)

OTHER PUBLICATIONS

De Ley et al. "Phasnnarhabditis hermaphrodita (Nematoda: Rhabditidae), a potential biocontrol agent isolated for the first time from invasive slugs in North America" Nematology 00 (2014) 1-10. (Year: 2014).*
(Continued)

*Primary Examiner* — Blaine Lankford
*Assistant Examiner* — Lauren K Van Buren
(74) *Attorney, Agent, or Firm* — Schwegman Lundberg & Woessner, P.A.

(57) ABSTRACT

A composition and methods of using the composition for the control of mollusks are provided, which include an effective amount of one or more isolated *Phasmarhabditis* nematodes, wherein at least one of the isolated nematodes is *P. californica*, *P. papillosa* or *P. hermaphrodita*, and wherein the *P. hermaphrodita* does not comprise *Moraxella osloensis*.

11 Claims, 18 Drawing Sheets

(51) Int. Cl.
  *A01P 9/00*   (2006.01)
  *A01N 25/08*  (2006.01)
  *A61K 39/07*  (2006.01)
  *A01N 25/00*  (2006.01)

(56) References Cited

FOREIGN PATENT DOCUMENTS

| KR | 101230787 B1 * | 2/2013 |
| NL | 1033726 C2 | 10/2008 |
| WO | WO-2014116378 A1 | 7/2014 |
| WO | WO-2014170364 A1 | 10/2014 |

OTHER PUBLICATIONS

International Application Serial No. PCT/US2016/054969, International Search Report and Written Opinion dated Dec. 30, 2016, 8 pgs.

Rae, R.G., et al., "Biological control of terrestrial molluscs using Phasmarhabditis hermaphrodita—Progress and prospects", Pest Management Science, 63 (Oct. 2, 2007) 1153-1164.

"European Application Serial No. 16852770.3, Extended European Search Report dated Feb. 25, 2019", 11 pgs.

De Ley, Irma Tandingan, et al., "Description of *Phasmarhabditis californica* n. sp. and first report of P. papillosa (Nematoda: Rhabditidae) from invasive slugs in the USA", Nematology, vol. 18, No. 2, (2016), 175-193.

Ross, Jenna L., et al., "The role of parasite release in invasion of the USA by European slugs", Biological Invasions, vol. 12, No. 3, (Apr. 14, 2009), 603-610.

Wilson, Michael J., et al., "Monoxenic culture of the slug parasite Phasmarhabditis hermaphrodita (Nematoda: Rhabditidae) with different bacteria in liquid and solid phase", Fund. Appl. Nematol., vol. 18, No. 2, (Feb. 1, 1995), 159-166.

"International Application Serial No. PCT US2016 054969, International Preliminary Report on Patentability dated Apr. 12, 2018", 7 pgs.

"European Application Serial No. 16852770.3, Invitation to Remedy Deficiencies Pursuant to Rule 30(3) EPC Rule 163(3) EPC dated May 25, 2018", 2 pgs.

"European Application Serial No. 16852770.3, Response filed Jul. 24, 2018 to Invitation to Remedy Deficiencies Pursuant to Rule 30(3) EPC Rule 163(3) EPC dated May 25, 2018", 4 pgs.

Canadian Application Serial No. 3,000,836, Examiner's Rule 30(2) Requisition dated Mar. 14, 2019, 4 pgs.

* cited by examiner

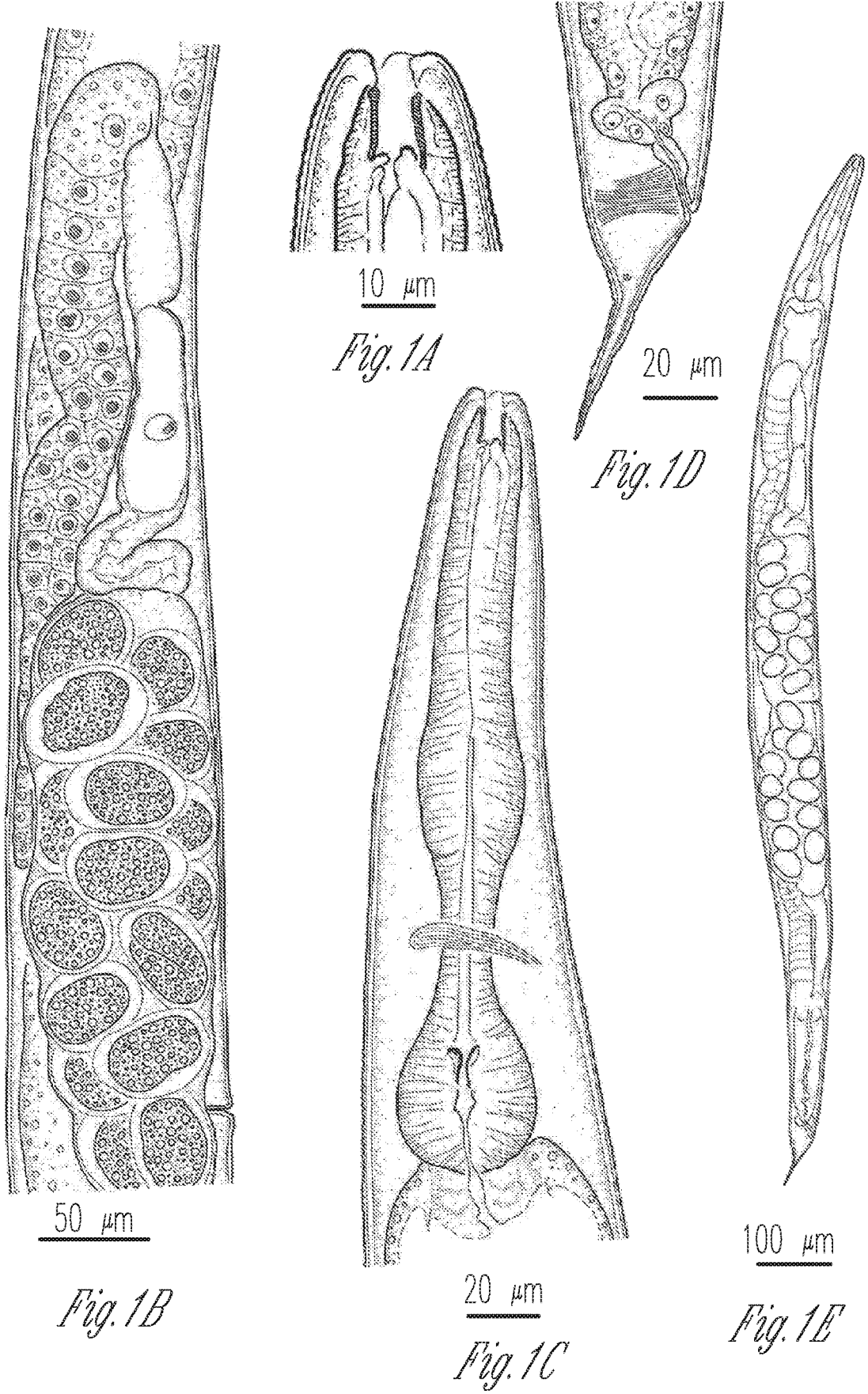

10 µm

50 µm

50 µm

50 µm

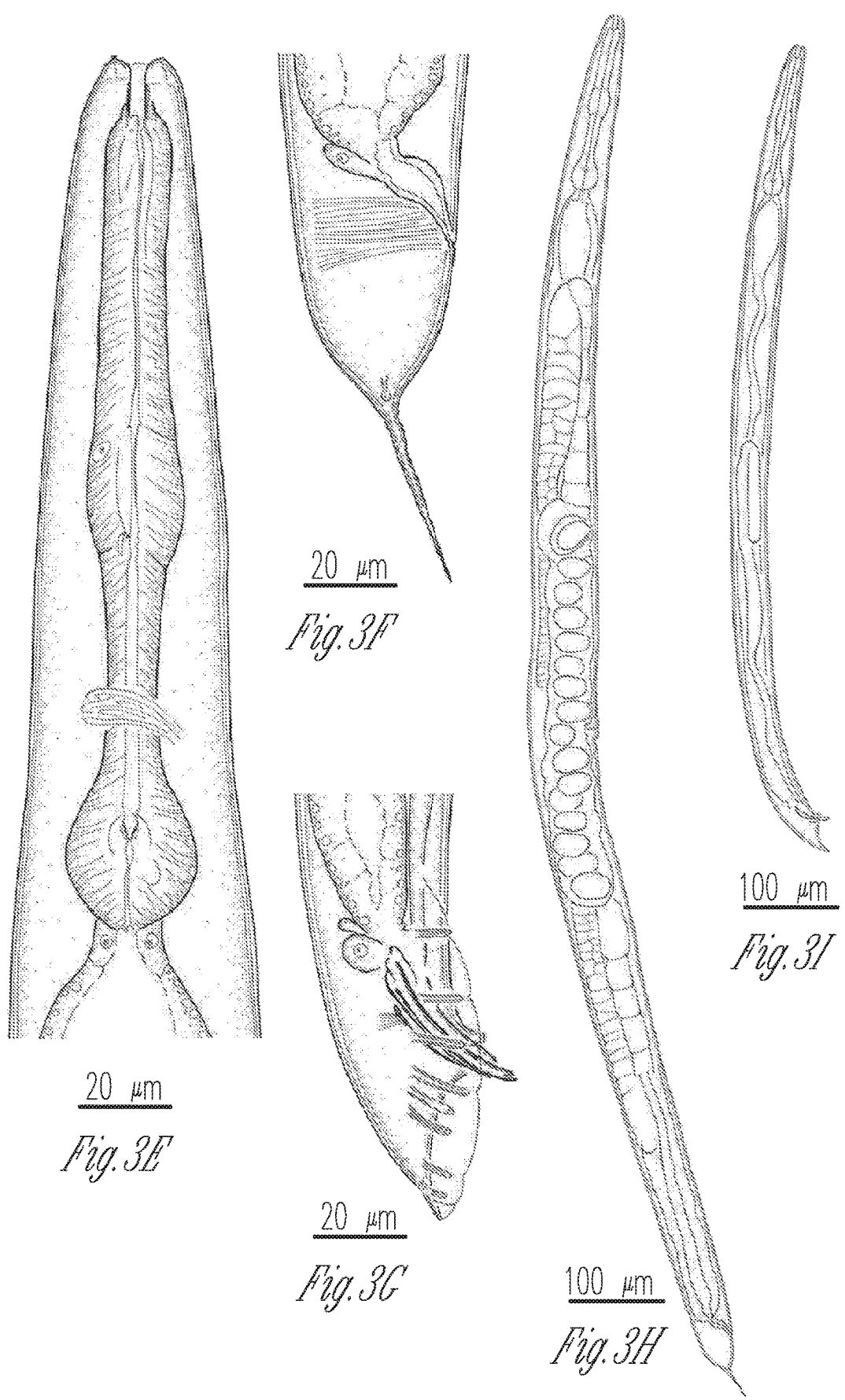

MOLLUSK-KILLING BIOPESTICIDE

CROSS-REFERENCE TO RELATED APPLICATIONS

This application is a U.S. National Stage Filing under 35 U.S.C. 371 from International Application No. PCT/US2016/054969, filed on Sep. 30, 2016, and published as WO 2017/059342 A1 on Apr. 6, 2017, which claims the benefit of the filing date of U.S. application Ser. No. 62/236,674, filed on Oct. 2, 2015, the disclosure of each of which is incorporated by reference herein in its entirety.

BACKGROUND

Invasive snails and slugs are among the most important pests of agriculture, and horticulture including high-value crops. They incur direct losses in crop yield and quality (fecal and mucus contamination) and increase management costs; and are vectors of plant and human pathogens, e.g., *Alternaria brassicicola*, pathogen of *brassica* dark leaf spot and *Angiostrongylus cantonensis* that causes eosinophilous meningo-encephalitis. Management of slugs and snails relies almost exclusively on molluscicides, with metaldehyde use currently being the standard practice. Although generally effective and efficient, it is very toxic to pets and under high relative humidity, activity is reduced and snail recovery possible. Iron phosphate and sodium ferric EDTA are often used in high humidity or where there are concerns about pet safety. However, iron phosphate may also be toxic to non-targets like earthworms. Methiocarb is a restricted use material and is toxic to mammals including humans, birds, bees and aquatic taxa. Other nonbiological control options, e.g., copper barriers, are impractical for large areas.

Following the rediscovery of *Phasmarhabiditis hermaphrodita* in the UK in 1996, *Phasmarhabditis* was reported in Chile (France and Gerding, 2000), Iran (Karimi et al., 2003), Egypt (Genena et al., 2009), New Zealand (Wilson et al., 2012), China (Huang et al., 2015; NCBI sequence data) and the USA (Tandingan De Ley et al., 2014). There are currently six nominal species of the genus with *P. hermaphrodita* having the widest host range and association with 15 gastropod families (see Grewal et al., 2002; Rae et al., 2007; Ross et al., 2011). *P. hermaphrodita* with bacteria *Moraxella osloensis* has been commercially sold as Nemaslug®, a biopesticide, in the UK and 14 European countries for over 20 years.

*P. hermaphrodita* was recently reported in California from three invasive slug taxa *Arion hortensis* agg., *Deroceras reticulatum* and *Lehmannia valentiana* (Tandingan De Ley et al., 2014). During the same gastropod survey, two other *Phasmarhabditis* species were recovered: *Phasmarhabditis papillosa* from a single *Deroceras reticulatum* specimen and a new species, *Phasmarhabditis californica* isolated from three slug taxa (*Arion hortensis* agg., *Deroceras reticulatum*, and *Lehmannia valentiana*).

Prior to the introduction of molecular tools, species diagnostics in *Phasmarhabditis* was based exclusively on: i) female tail shape and length; ii) appearance of the bursa and spicule length; iii) number and position of bursal papillae; and iv) frequency of males and host association. As with other nematode groups, few diagnostic morphological features define each species. Females of different species are difficult to separate morphologically and males are very rare except for *P. papillosa*. Additionally, papillar arrangement on the male bursa is known to be diverse within highly studied rhabditid model organisms *Caenorhabditis elegans* and *C. briggsae*, with male individuals of the latter exhibiting patterns typical of the former (Baird, 2001). This underscores the importance of finding stable taxonomic characters to define a species and of using a combined taxonomic approach for an efficient and accurate species diagnostics.

The discovery of *Phasmarhabditis* for the first time in the US and North America paved the way for studies on its biological control potential against invasive slugs and snails including one that has not been introduced to California but has become economically important in Florida and Hawaii.

SUMMARY

The disclosure provides for biological control of gastropods, e.g., slugs or snails, using one or more isolated *Phasmarhabditis* species having bacteria that are associated with toxicity to slug or snail growth or development. As described herein, the nematode *P. hermaphrodita* was recently found for the first time in the U.S. In addition, *P. papillosa* was recovered from a cadaver of *Deroceras reticulatum*, and a new species, described as *P. californica*, was also isolated from *Arion hortensis* agg., *D. reticulatum* and *Lehmannia valentiana* in the U.S. (Tandingan De Ley et al., 2015). *P. californica* and *P. papillosa* are characterized based on combined morphological (LM, SEM), morphometrical characters and molecular data. Sequences of the internal transcribed spacer region (ITSI, 5.8S, ITS2), nearly-complete small subunit (SSU) and D2-D3 expansion segments of the large subunit (LSU) rDNA, as well as the COI genetic sequences of the mitochondria were determined. Molecular phylogenies were inferred from concatenated DNA sequence alignments of SSU and the D2-D3. *P. californica* is hermaphroditic, with rounded to pyriform basal bulb and conoid tail constricted at one-third its length; *P. papillosa* is gonochoristic, with longer isthmus, pyriform basal bulb and longer, convex to dome-shaped spicate female tail constricted halfway along its length. Sequence analysis revealed eight unambiguous autapomorphies for *P papillosa* and three for *P californica*. Phylogenetic analyses placed the new species in a well-supported clade comprised of *Phasmarhabditis* species and other gastropod-parasitic taxa. Morphological characters, genetic distance, reproductive strategy, and nucleotide autapomorphies support new species status.

In one embodiment, a composition having one or more isolated *Phasmarhabditis* species, which in one embodiment, at least one of which has bacteria that are associated with toxicity to slug or snail growth or development. In one embodiment, the isolated *Phasmarhabditis* species for use in the compositions include but are not limited to *P. hermaphrodita, P. californica* and/or *P. papillosa*. For example, two or more of *P. hermaphrodita, P. californica* and/or *P. papillosa* are selected based on their combined increased efficiency and effectivity to control the most common invasive slugs and snails damaging specialty crops, other crops, urban landscapes, and home gardens. The first replicated trials showed mortality rates of up to 60% for the invasive slug *Lehmannia valentiana* and almost 100% on neonate Giant African Snail *Lissachatina fulica* nine days after exposure. Thus, the use of compositions having *Phasmarhabditis* allows for a more sustainable and safe biocontrol strategy, either alone or as a component of an integrated pest management (IPM) program for invasive gastropods. In one embodiment, the composition does not include one or more species of bacteria, e.g., does not include *Moraxella osloen-* sis. In one embodiment, the composition further comprises one or more species of bacteria, as discussed below.

The disclosure thus relates to a composition for the control of mollusks wherein an effective amount of one or more *Phasmarhabditis* nematodes, e.g., infective dauer larvae which have been cultured with a nematode growth promoting and optionally pathogenicity-enhancing bacterium, as well as optionally a carrier or encapsulation agent, are provided. In one embodiment, the bacterium may be any of the isolated strains of *Alcaligenes faecalis, Bacillus pumilus, B. safensis*, and *Ochrobactrum* sp. The composition may be used in the form of a water-dispersable powder comprising a carrier, e.g., a calcium montmorillonite clay. The nematode concentration in the water-dispersable powder may be from about $0.1 \times 10^6$ to about $2.0 \times 10^6$ per gram of total composition (wet weight), or from $0.3 \times 10^6$ to about $1.5 \times 10^6$ per gram of the total composition (wet weight).

The present disclosure provides for the use of one or more *Phasmarhabditis* species that include *P. hermaphrodita, P. californica* and/or *P. papillosa* for the control of agricultural and horticultural pests or human and animal health pests, especially mollusks. The organisms can be cultured to produce amounts sufficient for formulation into suitable compositions for application in the field, greenhouse or other production systems, and other places where snails and slugs are pests. Typical compositions for practical use utilize acceptable carrier materials such as peat, clays, and other solids or semi-solid carriers such as gel materials.

BRIEF DESCRIPTION OF THE FIGURES

*P. hermaphrodita* is a well-studied species, *P papillosa* is least studied, while *P. californica* is new to science. Hence, the latter two species are characterized and described below.

FIGS. 1A-E *Phasmarhabditis californica* female: (A) Lip region with characteristic stoma; (B) Vulval region and anterior uterus, and oviduct; (C) Anterior part of the body with characteristic pharynx; (D) Posterior region showing anus, short conoid tail and posterior, prominent phasmids; (E) body habitus.

FIGS. 3A-I. *Phasmarhabditis papillosa* female (A-F, H) and male (G, I): Lip region with characteristic stoma (A); reproductive system showing the gonad flexure (B) with developing oocytes; and (C) spermatheca with sperm, well-developed eggs in the uterus, and the vulva[[.]] (D) and opposing gonads of mature females. Anterior region (E) with characteristic muscular metacorpus and pyriform, valvular basal bulb; and posterior region (F) showing anus, cupula tail, pointed tail tip, and posterior, protruding phasmids. Short, conoid, open peloderan male tail (G) with nine pairs of genital papillae. Body habitus of female (H) and male (I).

DETAILED DESCRIPTION

Biology of *Phasmarhabditis hermaphrodita*

Figure 2C:
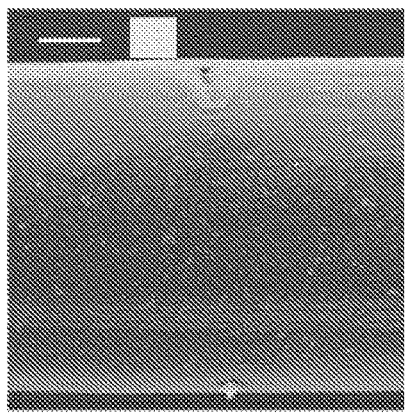
FIGS. 2A-E. SEM of *Phasmarhabditis californica* female: (A) Lip region; (B) Tail, lateral view; (C) Lateral field, midbody or vulval region; (D) Vulva, ventral view; (E) Ventral posterior region showing the tail, anus, and very posterior phasmids: (F) Enlarged and rotated view of UE).

The nematode is associated with a fatal disease in slugs with characteristic symptoms, most noticeably a swelling of the slug's mantle. The nematode was identified as belonging to the Sub-Order Rhabditina and further identified using a key (Andrassy, 1983). The main taxonomic characteristics of this group are the mouthparts and the male reproductive structures. The nematodes isolated at the then Long Ashton Research Station in the UK had a distinctive, short stoma with an isomorphic metastom, and males, when present, had peloderan bursas, fitting the genus *Phasmarhabditis*. Andrassy (1983) lists two species which are morphologically identical to these nematodes but are separated from each other on the basis of the number of males present in the populations. In *P. neopapillosa*, males and females are equally abundant, whereas in *P. hermaphrodita*, males are extremely rare. *P. hermaphrodita* was first described by Maupas, in Archives de Zoologie (1900), Vol 8 pp 464-624, who named the nematode *Rhabditis caussaneli*. He found resistant larval forms in the intestine of *Arion ater* which he collected in Normandy and maintained cultures of the nematode on rotten flesh for two years. He found that the adult worms were predominantly protandrous autogamous hermaphrodites. Males were present in very small numbers (1 male for 1300 females) and the number of males in cultures was not affected by nutritional conditions. Maupas never witnessed males mating with the females, which showed no change in their fecundity, or the sex ratio of their offspring in the presence of males. Maupas did not consider this nematode to be a parasite of slugs.

*P. papillosa* was first described by Schneider in Monographie der nematoden, Berlin, Germany, Verlag von Georg Reimer (1866), pp 153-154 as *Pelodera papillosa* with one paragraph describing the nematodes, few measurements; and an outline of the nematode anterior, pharynx and stoma, as well as the female and male tail with bursa. He provided only measurements for body length, a, b, and c values for females and male adults, and the vulval position. Mengert described *P. papillosa* (renamed *Rhabditis papillosa*), from *Arion empiricorum*, in his studies on the association between nematodes and terrestrial mollusks in Zeitschrift fur Morphologie and Okologie Tiere (1953), vol 41 pp 316-321. He also provided additional illustrations, including juveniles. There are no recent reports on the recovery nor the biology of *P. papillosa* since Mengert (1953).

In the same monograph (vol 41. pp 321-349), *P. neopapillosa* was described by Mengert, who named the nematode *Rhabditis neopapillosa*. He found the nematode as resistant larval stages ('dauer larvae') in the hind gut of the slug *Limax cinereoniger*. Mengert considered *P. neopapillosa* to be a saprophyte which thrives on decaying material for many generations, but when conditions become unfavorable the juveniles fail to mature and form resistant non-feeding dauer larvae. He hypothesized the lifestyle of *P. neopapillosa* to be identical to two other species, *P. papillosa* and *P. hermaphrodita*; and that the dauer larvae of these three species wander, when the opportunity arises, into the body of slugs where they remain as dauer larvae until the slug dies, after which they develop and reproduce, feeding on the corpse. Mengert thought that the stay in the slug was not a necessary part of the nematode life cycle but he considered that the dauer larvae of these species did show a degree of adaptation to life within slugs. However, he stated that they are not parasites of slugs.

Following the rediscovery of *P. hermaphrodita* in the UK, research on life cycle; bacterial associates and their effect on growth, dauer quality, and pathogenicity to *D. reticulatum*; as well as mass production, formulation and application were intensified (Rae et al., 2007). This led to the commercialization of *P. hermaphrodita* with *Moraxella osloensis* as a biological molluscicide called Nemaslug® in 1994 by MicroBio Ltd, a company that was later acquired by Becker Underwood, which in 2012 was acquired by BASF (Wilson and Rae, 2015). *P hermaphrodita* was found to be a facultative parasite and its pathogenicity on the host slug *D. reticulatum* was further established by Rae and colleagues (2010).

Nematodes can be isolated from slugs and snails collected from the field using traps e.g. bran baited traps left in an area of rough grassland or simply collected from under pieces of broken pots, wood, potted plants or other suitable sources of cover in production systems such as nurseries, and in home gardens. Once collected the nematodes can be isolated from the slug's gut or mantle cavity following dissection. Alternatively, snails and slugs collected from production systems are grown on an organic vegetable diet in boxes lined with moistened paper towels, and dead specimens are immediately placed on 1% plain agar for further observation of emerging nematodes.

Many species of nematodes are associated with snails and slugs (Mengert, 1953) and the identification of the nematodes may be confirmed using a taxonomic key (Andrássy, 1983) and molecular methods. If only immature stages e.g. first (J1), second (J2) or infective juveniles (dauer larvae, J3 or IJ) are found in the slug, it is necessary to perform DNA sequencing or culture the nematodes on agar to identify the species based on both DNA sequences and adult morphology and morphometry. In addition, there can be a combination of nematodes in a single mollusk, and species identification can be confounded by the morphological similarities of immature stages not only of the genus, *Phasmarhabditis*, but other taxa within Rhabditidae.

*Phasmarhabditis* nematodes have been isolated on a number of occasions in other countries. During our 2012-2013 surveys in Californian nurseries and garden centers, our recovery was approximately 1%. *P hermaphrodita* and *P. californica* are hermaphrodites while *P. papillosa* has frequent males in culture and mating is very frequent especially in young one week to two-week old cultures. In some cases the population of nematodes consisted of males and females, whereas in other cases the populations consisted of hermaphrodites only. Nematodes are examined using light microscopy and scanning electron microscopy. Before the introduction of polymerase chain reaction (PCR) and DNA sequencing as efficient tools for species diagnostics, the protein profiles from different populations were used to separate *P. hermaphrodita* and *P. neopapillosa* (Hooper et al., 1999).

As described in more detail below, three species of *Phasmarhabditis* were isolated from cadavers of four invasive slug taxa in California: two known species (*P. hermaphrodita* and *P. papillosa*) recovered for the first time in North America, and one new to science, *P. californica* n.sp. Recently, *P. californica* and *P. papillosa* are characterized based on combined morphological (LM, SEM), morphometrical characters and molecular data. Molecular phylogenies were inferred from concatenated DNA sequence alignments of nearly-complete SSU and the D2-D3 domains of the LSU rDNA. *P. californica* is hermaphroditic, with rounded to pyriform basal bulb and conoid tail constricted at one-third its length; *P. papillosa* is gonochoristic, with longer isthmus, pyriform basal bulb and longer, convex to dome-shaped spicate female tail constricted halfway along its length. Sequence analysis revealed 20 unambiguous autapomorphies for *P. hermaphrodita*, eight for *P. papillosa* and three for *P. californica* (Table 1A). Phylogenetic analyses placed the new species in a well-supported clade comprised of *Phasmarhabditis* species and other gastropod-parasitic taxa. Morphological characters, genetic distance, reproductive strategy, and nucleotide autapomorphies support the new species status.

*Phasmarhabditis* nematodes can be produced by methods to be described in this specification. It is already known in the art that insect parasitic nematodes can be produced on a large scale for commercial use by liquid culture, using stirred tank or airlift fermenters, or by solid culture in bags or trays of foam chips. Similar techniques can be used for large scale production of the nematodes. Thus the nematode used in accordance with this disclosure is readily cultured on kidney-based medium in foam chips or in liquid culture, using similar techniques to those used for production of insect parasitic nematodes and for the formulation of *P. hermaphrodita* and *M. osloensis* (Wilson et al. 1993). For the purposes of the present disclosure it is recommended that the culture of nematodes is harvested at the infective dauer juvenile stage.

Associated Bacteria

*Phasmarhabditis* nematodes are bacterial feeders. Many bacterial isolates have been found to be associated with *Phasmarhabditis* nematodes after isolation from moribund slugs.

In order to consistently produce high yields of *Phasmarhabditis* nematodes which are pathogenic to mollusks, they may be grown in monoxenic cultures, i.e., with one known associated bacterium. Bacteria capable of supporting nematode growth can be isolated from within nematodes, from nematode cultures growing on a mixed microbial population, from slugs infected with bacteria and from slug corpses infested with the nematodes. Nematodes can then be axenized, and introduced into cultures with the different individual species of bacteria. Incubation of these cultures allows the selection of bacterial isolates capable of supporting nematode growth.

Approximately 40 bacterial isolates/species representing 119 single colonies from a nematode collection have been isolated (Table 1A), each identified by sequencing the 16SrDNA.

TABLE 1A

List of bacteria associated with gastropod nematodes in culture.

| Item | Bacterial taxa | Frequency of isolates |
|---|---|---|
| 1 | *Achromobacter denitrificans* | 1 |
| 2 | *Achromobacter* sp. | 2 |
| 3 | *Alcaligenes faecalis* | 34 |
| 4 | *Alcaliegenes* sp. | 4 |
| 5 | *Bacillus cereus* | 1 |
| 6 | *Bacillus licheniformis* | 9 |
| 7 | *Bacillus niacini* | 1 |
| 8 | *Bacillus pumilus* | 5 |
| 9 | *Bacillus safensis* | 4 |
| 10 | *Bacillus subtilis* | 3 |
| 11 | *Brevibacterium* sp. | 1 |
| 12 | *Brevundimonas diminuta* | 5 |
| 13 | *Citrobacter freundii* | 1 |
| 14 | *Enterobacter* sp. | 1 |
| 15 | *Flavobacterium* sp. | 4 |
| 16 | *Herbaspirillum frisingense* | 1 |
| 17 | *Klebsiella oxytoca* | 1 |
| 18 | *Leucobacter chromiireducens* | 1 |
| 19 | *Microbacterium keratanolyticum* | 1 |
| 20 | *Microbacterium oxydans* | 3 |
| 21 | *Microbacterium resistens* | 4 |
| 22 | *Myroides odoratus* | 2 |
| 23 | *Ochrobactrum* sp. | 6 |
| 24 | *Paenibacillus* sp. | 2 |
| 25 | *Paenibacillus odorifer* | 1 |
| 26 | *Pseudochrobactrum* sp. | 1 |
| 27 | *Pseudochrobactrum saccharolyticum* | 5 |
| 28 | *Pseudomonas composti* | 1 |
| 29 | *Pseudomonas protegens* | 1 |

TABLE 1A-continued

List of bacteria associated with gastropod nematodes in culture.

| Item | Bacterial taxa | Frequency of isolates |
|---|---|---|
| 30 | *Pseudomonas putida* | 2 |
| 31 | *Pseudomonas* sp. | 3 |
| 32 | *Pusillimonas* sp. | 1 |
| 33 | *Rheinheimera tangshanensis* | 1 |
| 34 | *Rhodococcus erythropolis* | 1 |
| 35 | *Sphingobacterium mizutaii* | 1 |
| 36 | *Sphingobacterium* sp., *Sphingobacterium composti* | 1 |
| 37 | *Stenotrophomonas maltophilia* | 2 |
| 38 | *Stenotrophomonas* sp. | 1 |

Jackson et al., 2015. Identification based on 16S rRNA gene

Table 1B provides isolates of *P. californica*, *P. hermaphrodita*, and 1 of *P. papillosa*.

TABLE 1B

| *Phasmarhabditis* species | Accession/ Lab Code |
|---|---|
| *P. hermaphrodita* | ITD056 |
|  | ITD207 |
|  | ITD272 |
|  | ITD290 |
| *P. californica* | ITD046 |
|  | ITD059 |
|  | ITD235 |
|  | ITD236 |
|  | ITD291 |
|  | ITD724 |
|  | ITD726 |
|  | ITD727 |
|  | ITD728 |
|  | ITD729 |
|  | ITD730 |
| *P. papillosa* | ITD510 |

*Phamarhabditis californica* ITD726 was deposited under accession number PTA-126597 on 02-05-2020 at the American Type Culture Collection (ATCC), 1801 University Boulevard, Manassas, Va. 20110-2209, a recognized public depository for strains of microorganisms, in accordance with the Budapest Treaty in the International Recognition of the Deposit of Microorganisms for the Purposes of Patent Procedure The ability of nematodes reared on different species of bacteria to kill slugs can be tested in a bioassay. In such a bioassay slugs are exposed to different numbers of nematodes and the resulting slug mortality is recorded. Using this method, quantitative measures of pathogenicity (e.g., $LD_{50}$) of nematodes against slugs can be obtained and used to compare the pathogenicity of nematodes reared on different species of bacteria. It is important that the nematode is supplied in association with specific bacteria because bacteria are essential not only for growth of the nematode (both in vitro and in vivo) but may also contribute to their ability to kill slugs. The nematode carries associated bacteria on entry into the slug thus allowing rapid establishment and multiplication of the nematode leading to the death of the slug.

To test the virulence of bacterial associates in our collection, we selected six isolates, representing four species that were found to support good nematode growth on agar and had the highest frequency of recovery and/or association with *Phasmarhabditis* spp. These were: *Bacillus pumilus* (BP-ITD272), *B. safensis* (BS-ITDB272), *Ochrobactrum* sp., and *Alcaligenes faecalis* (AF-ITDB235, AF-ITDB290 and AF-ITDB510). *A. faecalis* was the most prevalent bacteria among gastropod nematodes and was also associated with all three *Phasmarhabditis* species.

*Alcaligenes faecalis* is a Gram-negative bacterium, rod-shaped, motile, non-nitrate reducing, oxidase positive, catalase positive, alpha hemolytic, and citrate positive (variable) obligate aerobe that is commonly found in the environment. *A. faecalis* subsp. *faecalis* strain NCIB 8687 is reported as an arsenite-oxidizing bacteria; *A. faecalis* strain MOR02, isolated from an entomopathogenic nematode recovered from soil samples in Morelos, Mexico, is associated with the nematodes *Steinernema feltiae*, *S. carpocapsae*, and *Heterorhabditis bacteriophora*, and causes 96% mortality to *Galleria mellonella* larvae (Queroz-Castañeda, et al., 2015).

*Bacillus pumilus* is a Gram-positive, aerobic, spore-forming *Bacillus* commonly found in the soil (Priest 1993). *B. pumilus* contains one circular chromosome including about 4000 genes and 3600-3900 proteins with varying length in the range of 3.7 to 3.8 Mbp. 41% of the DNA base pairs in *B. pumilus* are G-C. The cellular structure of *B. pumilus* is similar to other *Bacillus* species, i.e., the outer layer of the peptidoglycan cross-links in *B. pumilus* is covered by teichoic and lipoteichoic acids same as the most other Gram positive bacteria. These acids contains polyglycosyl phosphates with mono- and disaccharides as their monomers that can play a role in adhesion to different surfaces like the host cells (Parvathi, 2009; Potekhina, 2011).

*Bacillus safensis* is a Gram-positive, spore-forming, rod bacterium, and an aerobic, chemoheterotroph. Cell size ranges from 0.5-0.7 μm in diameter and 1.0-1.2 μm in length (Satomi et al., 2006). Bacteria are motile, and use polar flagella for locomotion. Cells are considered mesophillic, as they can grow in temperatures ranging between 10-50° C. *Bacillus* safensis FO-036b has an optimal temperature range from 30-37° C., and cannot grow at 4 or 55° C. *Bacillus* safensis FO-036b prefers 0-10% salt, and a pH of 5.6. This strain was also found to produce spores that are resistant to hydrogen peroxide and UV radiation (Tirumalai, et al., 2013).

Useful variants of bacteria listed herein may be obtained by repeated sub-culturing of pure cultures of these strains. Variants may also be obtained either by re-isolating bacteria from *Phasmarhabditis* nematodes previously grown in association with either of the strains or by re-isolating bacteria from slugs infected with nematodes. Such variants may have incurred genotypic or phenotypic changes as a result of environmental influences or selective pressure. Useful derivatives of *Bacillus pumilus* (BP-ITD272), *B. safensis* (BS-ITDB272), *Ochrobactrum* sp., and *Alcaligenes faecalis* (AF-ITDB235, AF-ITDB290 and AF-ITDB510) may be constructed by the introduction of DNA coding for desirable attributes from other organisms. Methods for introduction of foreign DNA into bacteria are well known to those skilled in the art and include techniques such as plasmid transfer, transduction and transfection. Useful mutants of *Bacillus pumilus* (BP-ITD272), *B. safensis* (BS-ITDB272), *Ochrobactrum* sp., and *Alcaligenes faecalis* (AF-ITDB235, AF-ITDB290 and AF-ITDB510) may be obtained by mutagenesis using methods, well known to those skilled in the art, such as chemical (e.g., nitrosoguanidine), physical (ultraviolet light) and genetic (transposon mutagenesis) techniques. Such variants, derivatives and mutants of the strains may be altered with respect to characteristics such as growth rate or the ability to grow on certain food sources but will retain the essential characteristics relevant to this disclosure, i.e., the ability to both support growth of *Phasmarhabditis* nematodes and optionally to enhance pathogenicity towards mollusks.

For use in control of agricultural pests, nematodes are harvested from fermenters by centrifugation, filtration or settling under gravity. The nematodes are washed to remove spent medium components and either formulated immediately or stored as cooled, aerated aqueous suspensions prior to subsequent formulation. Nematodes can be formulated for agricultural use as aqueous suspensions, on solid carriers such as charcoal, clays, peat, vermiculite or polyetherpolyurethane sponge, or encapsulated in gels such as alginate or polyacrylamide. A particularly desirable formulation contains desiccated or partially-desiccated nematodes. The formulated nematodes can be applied for control of pests by forming an aqueous suspension and applying this to the area to be treated by spray, irrigation or drench. The nematode containing composition can be applied before soil cultivating, preplant or during planting.

The invention will be described by the following non-limiting examples.

Example 1

Materials and Methods
Collection and Maintenance of Gastropods

Eleven gastropod collections were made under a California Department of Food and Agriculture (CDFA) permit in plant nurseries and garden centers throughout California (Tandingan De Ley et al., 2014). Slug and snail specimens obtained from outside Riverside County were grown separately at the University of California Riverside Insectary and Quarantine facility. All gastropods were grown on organic carrots in plastic containers lined with moist paper towels. Food and towels were replaced twice weekly.

Identification of Nematodes

Dead slugs and snails were immediately placed on 1% plain agar (PA) and emerging nematodes were grown on both PA and nutrient agar in axenic cultures and subsequently sub-cultured until ready for identification.

Nematodes from cultures were processed to anhydrous glycerin (Seinhorst, 1959 as modified by De Grisse, 1969) for light microscopy. Morphological (light microscopy and scanning electron microscopy) and morphometrical data as well as DNA sequencing for ribosomal RNA (small subunit or SSU, D2-D3 domains of the large subunit or LSU) were performed as previously described (Tandingan De Ley et al., 2014).

Molecular Phylogenetic Analyses

Additional sequences of nematode taxa were downloaded from GenBank and a secondary structure alignment was created based on existing secondary structure models of nearly complete SSU and partial D2-D3 LSU rRNA genes. Secondary structure annotation of SSU rRNA genes of species was based on the European ribosomal RNA Database (Wuyts et al., 2004). Published models of the secondary structure of the LSU rRNA gene for *Caenorhabditis elegans* and *Labiostrongylus bipapillosus* (Chilton et al., 2003; Ellis et al., 1986; Gutell & Fox, 1988) were used as a basis for alignment and annotation of the D2-D3 sequences. Secondary structure annotation was manually added to non-annotated sequences using 4SALE (Seibel et al., 2006), and all sequences were manually aligned to maximize apparent positional homology of nucleotides.

The concatenated alignment was analyzed with Bayesian phylogenetic inference using the mcmcphase program in the PHASE package (Gowri-Shankar & Jow, 2006; Version 2.0)

with *Mesorhabditis anisomorpha* sp as outgroup based on previously published SSU phylogenies (Van Megen et al., 2009). The entire concatenated alignment was partitioned into SSU and LSU. Furthermore, each partition was divided into secondary partitions of "stems" (paired sites) and "loops" (non-paired sites) to account for the potential phylogenetic importance of compensatory substitutions. The REV nucleotide substitution model (Tavare, 1986) was used for non-paired sites, whereas RNA7A (Higgs, 2000) nucleotide substitution model was used for paired sites. Model parameters were estimated independently for all sub-partitions (non paired and paired sites of SSU and non paired and paired sites of LSU). Chains were allowed to burn in for 500,000 generations, followed by 5 million generations (total 5.5 million generations) during which tree topologies, branch length and model parameters were sampled every 200 generations.

Description for *Phasmarhabditis californica* (Isolate ITD236)

Female (Table 2)

Figure 2F:
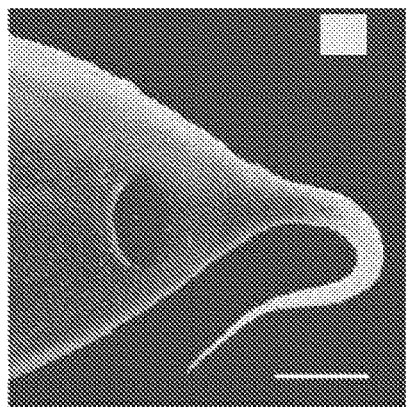
Figure 2B:
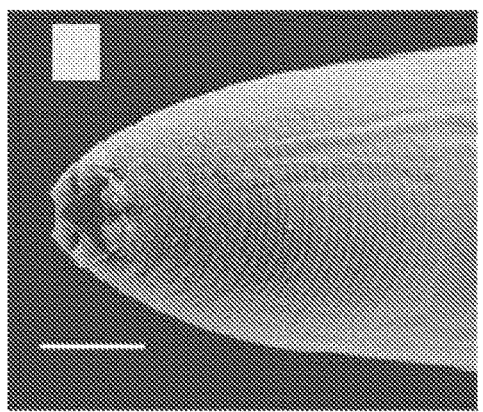
Figure 2E:
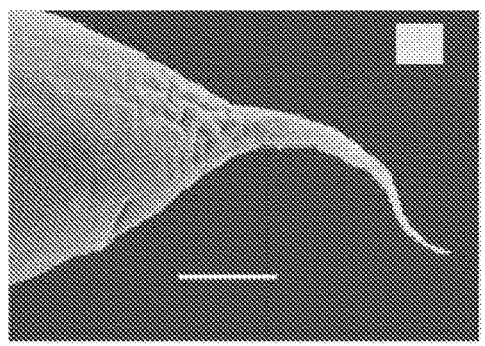
Figure 2A:
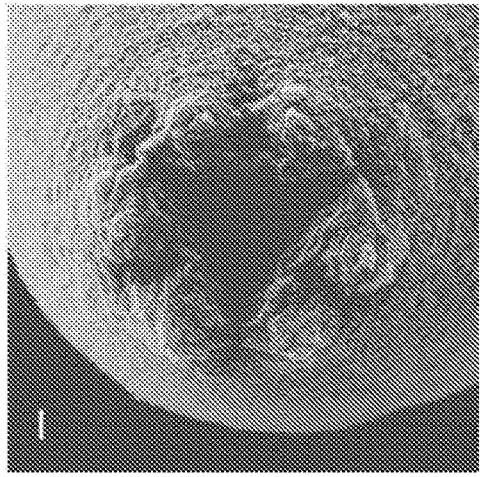
Figure 2D:
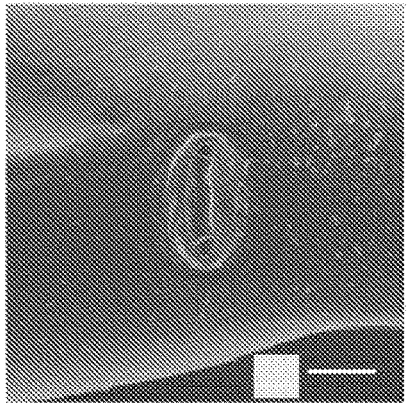

Body 1.3-1.8 mm long, cylindrical, almost straight or slightly curved in the middle when relaxed by heat (FIG. 1E). Annules fine and less prominent under light microscope. Lateral field with six (SEM) prominent incisures. Anterior end bluntly rounded, lip region 16 (12-18) µm wide, continuous with body, six lips grouped in pairs (FIG. 2 A,B). One labial papilla protruding anteriorly from each lip with a clearly demarcated inner labial dendrite emerging apically (FIG. 2B). A smaller subapical protrusion of a second dendrite ending visible only on lips with cleanest papillar surfaces, analogous to the rootleted inner labial dendrite below the papillar surface in *Caenorhabditis elegans* (Ware et al., 1975). Two less prominent outer cephalic papillae on dorsal lip pair and one each on subventral pairs. Amphid opening is a small slit opening laterally near outer margin of each lateral lip. Mouth triangular (FIG. 2A,B) with slightly convex sides. Stoma 19 µm long, about as long as lip region diam., distinct cheilostom, gymnostom, and stegostom with mean lengths of 4, 3 and 11 µm, respectively. Stegostom ending with well developed, rounded, isomorphic metarhabdions, each with three minute tubercles. Corpus cylindrical (FIG. 1C), 2.5 times as long as isthmus with slightly enlarged non-valvular metacorpus narrowing into isthmus and a bulbous post-corpus with striated valvular apparatus. Nerve ring surrounding the isthmus at 70% of the neck length. Deirids not prominent. Excretory pore very posterior, opening at middle or near base of terminal bulb. Cardia conoid. Reproductive system didelphic, amphidelphic, ovaries reflexed with tips sometimes reaching level of vulva (FIG. 1B). Anterior and posterior ovaries as measured from vulva to anterior/posterior flexure, occupying 25% anterior and posterior to the vulva. Numerous sperm in oviducts despite absence of males. Uteri of mature females often filled with round oocytes commonly hatching inside the body (FIG. 1B). Vulva a transverse slit halfway along the body. Vagina length variable, often extending past middle of vulval body diam. Intestine ending in a rectum 0.9-1.9 anal body diam. long with three cell bodies of associated sphincters (FIG. 1D). Anus an arcuate slit (FIG. 2F). Anal body diam. 36% of tail length. Phasmids prominent, position variable, located at 32 (27-48) % of tail length. Tail conoid (FIGS. 1D, E and 2E,F), wider part forming 38 (28-54)% of tail length, hyaline tail tip longer.

Male

No males were found from any of the four isolates.

Type Locality and Habitat

Type specimens were obtained from subcultures of nematodes that emerged from a cadaver of *D. reticulatum* that was collected from Eureka, Calif., USA. In conformity with the system used by *Caenorhabditis* Genetics Center, this isolate is designated ITD046, and other isolates of this species are designated ITD059, ITD235, ITD236 and ITD291.

Type Material

Holotype female (slide 31479) and female paratypes (slide 31480) deposited at the Nematode Collection of the University of California, Riverside, USA; and female paratypes (slides 104308 and 104309) at the Nematode Collection of the Zoology Museum, Ghent University, Belgium.

TABLE 2

Comparative measurements for three species of Californian *Phasmarhabditis* versus *P. neopapillosa* and *P. tawfiki*.

| | *Phasmarhabditis* spp *Phasmarhabditis* species in California | | | | |
|---|---|---|---|---|---|
| Characters/ Morphometrics | *Phasmarhabditis californica* ITD 236 female (n = 20) | *Phasmarhabditis californica* ITD 236 holotype female | *Phasmarhabditis papillosa* ITD 510 female (n = 20) | *Phasmarhabditis papillosa* ITD 510 male (n = 12) | *Phasmarhabditis hermaphrodita* ITD272 female, US (n = 10) |
| Body length | 1500.8 ± 116.6 (1298.0-1756.6) | 1460.7 | 1590.3 ± 195.5 (1202-1932) | 1233 ± 184.5 (1011-1565) | 1542.2 ± 161.2 (1283.9-1721.0) |
| a (L/gbw) | 18.9 ± 2.9 (15.1-23.1) | 14.2 | 19.9 ± 1.7 (16.0-22.7) | 20.8 ± 2.6 (15.6-24.4) | 17.2 ± 1.6 (15.1-19.5) |
| b (L/ant-cardia) | 7.0 ± 0.4 (6.3-8.0) | 6.8 | 7.1 ± 0.9 (5.4-9.0) | 6.5 ± 0.9 (5.5-7.8) | 8.0 ± 0.6 (6.9-8.9) |
| C (L/tl) | 18.3 ± 2.2 (14.1-22.5) | 19.2 | 15.5 ± 4.3 (10.9-26.3) | 29.2 ± 7 (23.2-49.5) | 15.6 ± 1.2 (13.4-17.4) |
| c' (L/abw) | 2.8 ± 0.5 (2.4-4.0) | 2.6 | 2.8 ± 0.5 (1.9-3.6) | 1.2 ± 0.3 (0.6-1.5) | 2.5 ± 0.2 (2.2-3.0) |
| Greatest body width | 81.1 ± 12.3 (60.2-99.1) | 96.8 | 81 ± 14.6 (57.2-116.1) | 60.8 ± 15.7 (45.3-88.5) | 90.0 ± 8.3 (82-107) |
| Lip region width | 16.0 ± 1.8 (12.4-18.0) | 12.7 | 15.9 ± 1.7 (13.4-19.7) | 13.5 ± 2.1 (10.8-17.9) | 17.7 ± 1.9 (14.1-20.4) |
| Stoma L | 18.8 ± 2.1 (16.0-21.5) | 19.3 | 19.9 ± 2.4 (16.4-25.2) | 18.4 ± 2.4 (16.0-22.2) | 18.4 ± 1.0 (17.0-20.3) |
| cheilostom | 4.4 ± 0.9 (3.2-6.0) | 5.8 | 5.6 ± 1.1 (3.0-7.3) | 5.0 ± 0.5 (4.2-6.2) | 4.0 ± 0.5 (3.4-4.9) |

TABLE 2-continued

Comparative measurements for three species of Californian *Phasmarhabditis* versus *P. neopapillosa* and *P. tawfiki*.

| | | | | | |
|---|---|---|---|---|---|
| gymnostom | 3.5 ± 0.8 (2.3-5.2) | 5.1 | 4.1 ± 0.8 (3.0-5.6) | 3.3 ± 0.5 (2.7-4.2) | 3.2 ± 0.9 (2.1-4.9) |
| stegostom | 11.0 ± 1.8 (8.2-13.4) | 8.0 | 11.8 ± 2.8 (7.6-17.0) | 10.1 ± 1.9 (8.1-13.0) | 11.3 ± 1.1 (10.1-12.9) |
| Procorpus | 69.4 ± 7.2 (52.1-77.7) | 66.2 | 90.1 ± 7.6 (72.3-101.4) | 58.2 ± 11.3 (46.1-79.9) | 62.3 ± 2.5 (57.1-65.6) |
| Metacorpus | 39.0 ± 5.2 (31.1-46.4) | 46.4 | 26.2 ± 2.8 (21.5-34.9) | 38.7 ± 5 (31.9-46.8) | 35.1 ± 6.4 (25.1-44.8) |
| cardia | 12.2 ± 3.2 (7.4-17.1) | 16.2 | 8.5 ± 2.2 (4.3-11.0) | 9.3 ± 2.5 (6.2-14.5) | 8.5 ± 1.9 (5.1-11.5) |
| Corpus length | 108.0 ± 9.0 (83.2-119.4) | 112.7 | 115.9 ± 7.5 (102.1-129.9) | 92.23 ± 9.42 (79.9-108.9) | 97.4 ± 6.1 (86.5-106.6) |
| Metacorpus width | 29.9 ± 3.3 25.7-37.5 | 30.0 | 26.2 ± 2.8 (21.5-34.9) | 23.7 ± 5 (19.9-36.7) | 35.1 ± 6.4 (25.1-44.8) |
| Isthmus length | 42.7 ± 4.1 (37.4-49.2) | 38.0 | 58.6 ± 3.7 (45.6-63.4) | 49.8 ± 5 (43.8-58.3) | 42.7 ± 3.5 (37.3-48.2) |
| Basal bulb length | 45.3 ± 2.3 (41.6-49.3) | 44.4 | 65.5 ± 24.7 (34.6-102.6) | 35.8 ± 5.4 (27.0-44.5) | 36.9 ± 4.4 (32.1-45.9) |
| Basal bulb width | 39.5 ± 2.5 (35.2-43.5) | 40.1 | 40.1 ± 4.2 (34.1-49.4) | 30.7 ± 4.6 (24.6-39.5) | 29.6 ± 1.9 (27.2-32.4) |
| Neck length[3] | 213.2 ± 12.5 (180.1-230.3) | 214.4 | 225.6 ± 12.4 (190.3-246.8) | 189.6 ± 20 (133.0-210.7) | 193.4 ± 9.3 (175.2-209.1) |
| Nerve ring position | 149.4 ± 13.3 (115.2-164.9) | 145.0 | 168.0 ± 6.5 (151.6-178.2) | 139.1 ± 15.1 (95.1-151.5) | 139.5 ± 7.2 (126.3-149.1) |
| Excretory pore position | 196.9 ± 6.6 (187.1-204.2) | 196.0 | 187.3 ± 13.7 157.1-207.6 | 169.9 ± 3 (167.8-172) | (169.4-205.2) |
| G1% | 25.9 ± 3.3 22.3-32.8 | 32.8 | 25.2 ± 4.6 17.7-35.0 | | 24.2 ± 1.9 20.7-26.5 |
| G2% | 25.5 ± 4.3 17.8-32.5 | 32.5 | 25.2 ± 3.5 19.3-31.0 | | 26.7 ± 2.7 22.0-31.7 |
| RTL (male) | | | | 832.5 ± 213.9 521.8-1141.9 | |
| Vagina length/vbw % | 30.7 ± 25.8 (18.2-69.0) | 52.0 | 54.0 ± 6.6 (42.8-61.5) | | 30.2 ± 5.9 (23.3-33.6) |
| Vulva body width | 80.7 ± 11.8 (60.2-96.7) | 95.9 | 60.3 ± 13.4 (60.3-109.5) | | 89.2 ± 8.5 (79.9-106.6) |
| Anus to phasmid | 26.8 ± 7.8 (17.6-43.8) | 22.9 | 37.5 ± 8.2 (23.4-51.1) | 27.7 ± 4.2 22.4-32.6 | 47.0 ± 9.7 (38.0-70.1) |
| Rectum length | 38.8 ± 7.3 (27.3-48.7)) | 27.3 | 34.7 ± 4.3 (30.0-45.8 | | 39.1 ± 5.3 (33.6-52.3) |
| Tail length | 82.9 ± 8.9 (66.2-93.7) | 76.0 | 106.3 ± 16.5 (73.4-129.7) | 43.4 ± 7.5 28.4-52.2) | 99.0 ± 10.4 (85.4-117.2) |
| Anal body diam. (ABD) | 29.7 ± 4.1 (22.2-38.6)) | 30.0 | 38.4 ± 3.9 (31.3-44.5) | 37.5 ± 7.5 30.2-49.5 | 39.5 ± 4.3 (34.0-48.2) |
| Wide part tail | 34.8 ± 8.9 (24.2-50.1) | 25.3 | 44 ± 8.0 (30.2-60.7) | | 54.9 ± 12.1 (42.5-82.7) |
| Spicule length[4] | | | | 56.1 ± 7.1 (46.7-66.8) | |
| Gubernaculum length[4] | | | | 27.7 ± 5.2 (22.4-37.3) | |
| ABD/TL | 35.8 ± 5.1 (25.1-41.9) | 39.0 | 36.9 ± 7.2 (27.8-53.0) | 90.5 ± 29.7 (64.9-164.1) | 40 ± 3.2 33.3-45.0 |
| St L/LRW | 1.2 ± 0.2 (1.0-1.5) | 1.5 | 1.4 ± 0.2 (0.9-2.0) | 1.4 ± 0.4 (0.9-2.0) | 1.1 ± 0.2 (0.9-1.4) |
| Nring (% NL) | 69.8 ± 3.0 (64.0-74.0) | 67.6 | 71.5 ± 2.3 (68.0-75.2) | (70.3-78.3) 85.9 ± 4.3 | 72.2 ± 2.9 (67.2-75.4) |
| Epore (% NL) | 91.4 | 91.4 | 84.4 ± 3.7 (80.4-87.7) | (82.9-88.9) | |
| V (VP as % L) | 52.0 ± 0.9 (50.8-53.7) | 53.3 | 49.9 ± 2.5 (40.5-52.8) | | 50.4 ± 1.5 (48.2-52.9) |
| G (RTL as % L) | 50.0 ± 5.1 (44.0-58.4) | 65.2 | 49.7 ± 6.7 (41.2-63.9) | 66.5 ± 10.5 (48.3-76.5) | 50.9 ± 4.0 (46.1-56.8) |
| Rectum L/ABD | 1.4 ± 0.3 (0.9-1.9)) | 0.9 | 0.9 ± 0.1 (0.7-1.1) | | 1.0 ± 0.1 (0.8-1.3) |
| Phasmid (% TL) | 32.0 ± +6.8 26.5-47.6) | 30.1 | | 77.4 ± 12.0 (66.5-90.2) | 47.1 ± 5.8 (41.6-62.9) |
| Phasmid (% wide part TL) | 90.3 | 90.3 | 84.4 ± 5.8 (71.7-95.3) | | |
| Wide part tail (% TL) | 37.6 ± 15.4 27.8-54.4 | 33.3 | 41.7 ± 5.9 (32.9-54.2) | | 45.6 ± 25.1 49.8-74.2 |

TABLE 2-continued

Comparative measurements for three species of Californian *Phasmarhabditis* versus *P. neopapillosa* and *P. tawfiki*.

| Characters/ Morphometrics | *Phasmarhabditis* spp *Phasmarhabditis* species elsewhere | | |
|---|---|---|---|
| | *Phasmarhabditis hermaphrodita*[1,] female, UK n = 20 | *Phasmarhabditis neopapillosa*[1] female, UK n = 20 | *Phasmarhabditis tawfiki*[2] female, Egypt n = 20 |
| Body length | (1354 ± 115) 1186-1525 | 2227 ± 190 1817-2449 | 1715.9 ± 346.92 1150-2370 |
| a (L/gbw) | 15.2 ± 1.6 (12.4-17.9) | (16.0 ± 1.8) 14.6-16.2 | 17.3 ± 2.5 12-20 |
| b (L/ant-cardia) | 5.9 ± 0.4 (5.1-6.4) | 7.7 ± 0.5 7.2-8.4 | 6.5 ± 1 4.9-8.7 |
| C (L/tl) | 13.1 ± 0.7 (11.6-14.3) | 14.2 ± 1.2 12.1-16.9 | 11.1 ± 3.3 5.9-15.6 |
| c' (L/abw) | 2.9 ± 0.2 2.4-3.2 | 3.9 ± 0.5 3.3-5.0 | |
| Greatest body width | (90 ± 11.2) 75-106 | (141 ± 19.2) 101-174 | 95.5 ± 13.2 70-110 |
| Lip region width | 18 ± 0.7 (17-19) | 19 ± 0.5 18-19 | 18.7 ± 2.4 17-20 |
| Stoma L | 18 ± 1.3 16-21 | 21 ± 1.2 19-24 | 20.4 ± 1.74 17-24 |
| cheilostom | | | |
| gymnostom | | | |
| stegostom | | | |
| Procorpus | | | |
| Metacorpus | | | |
| cardia | | | |
| Corpus length | (107 ± 5.2) 96-114 | 144 ± 10.7 126-168 | 125.9 ± 18.41 100-156 |
| Metacorpus width | | | |
| Isthmus length | 59 ± 3.4 (54-63) | 76 ± 6.8 65-85 | 64.4 ± 8.34 48-80 |
| Basal bulb length | 35 ± 2.2 (31-40) | 57 ± 5.8 (48-62) | 47.65 ± 7.31 36-60 |
| Basal bulb width | | | |
| Neck length[3] | | | |
| Nerve ring position | 141 ± 6.9 (131-154) | 188 ± 11.3 168-205 | 167.6 ± 37.6 135-200 |
| Excretory pore position | 172 ± 12.5 157-189 (139-171) | 216 ± 10.6 199-231 | 222.5 ± 24.2 165-270 |
| G1% | 27 ± 1.7 24-30% | 34 ± 2.8 31-39% | 31.5 ± 7.3 21-46 |
| G2% | 29 ± 2.9 22-34% | 33 ± 2.6 29-37% | 30.1 ± 7.5 21-44 |
| RTL (male) | | | |
| Vagina length/vbw % | | | |
| Vulva body width | | | |
| Anus to phasmid | | | |
| Rectum length | | | |
| Tail length | 104 ± 8.6 (82-113) | 157 ± 15.3 (141-174) | 128 ± 22.7 85-140 |
| Anal body diam. (ABD) | | | |
| Wide part tail | | | |
| Spicule length[4] | | 68 ± 2.8 (60-71) | |
| Gubernaculum length[4] | | 33 ± 1.7 (31-37) | |
| ABD/TL | | | |
| St L/LRW | | | |
| Nring (% NL) | | | |
| Epore (% NL) | | | |
| V (VP as % L) | | | |
| G (RTL as % L) | | | |
| Rectum L/ABD | | | |
| Phasmid (% TL) | | | |

TABLE 2-continued

Comparative measurements for three species of Californian *Phasmarhabditis* versus *P. neopapillosa* and *P. tawfiki*.

Phasmid (% wide part TL)
Wide part tail (% TL)

[1]Based on Hooper et al. (1999).
[2]Based on Azzam (2003)
[3]Equivalent to pharynx measurement in Hooper et al. (1999).
RTL-male reproductive tract length, excluding flexure;
G1/G2 Vulva to anterior/posterior flexure of gonad as % of body length in female.
Corpus length (CL): measured along curvature of the lumen;
neck length (NL): from anterior end to the base of the basal bulb, measured along middle of the body;
reproductive tract length (RTL): measured along body axis, from anteriormost tip to posteriormost tip, i.e. excluding all flexures;
stoma length: from cheilorhabdia to base of the stoma.
Stoma terminology (cheilostom, gymnostom, and stegostom) was adapted from De Ley et al. (1995), and terminology associated with the structures of the nematode's anterior is based on Rashid et al. (1988).
[4]Based on Hooper et al. (1999) for *Phasmarhabditis neopapillosa*.

Redescription for *Phasmarhabditis papillosa* (ITD510)
Female (Table 2)

Figure 3A:
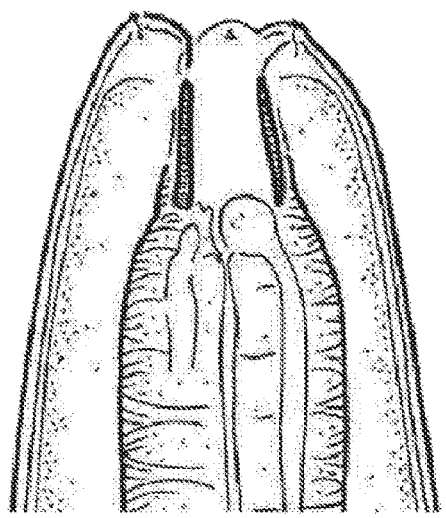
Figure 3B:
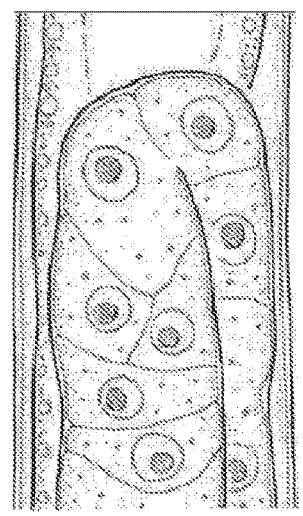
Figure 3C:
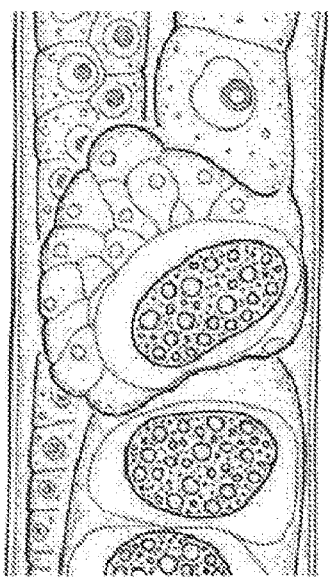
Figure 4D:
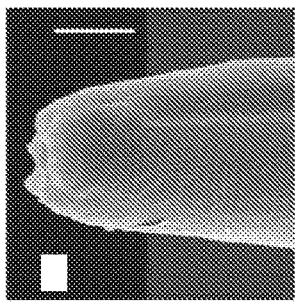
FIGS. 4A-H. SEM of *Phasmarhabditis papillosa* male (A-D) and female (E-H) anterior region. En face view (A-C) showing the lip region, triangular mouth, inner labial papillae and prominent outer cephalic papillae. Lateral field, pre-vulval region (G, H) and anterior region (D-F).
Figure 4H:
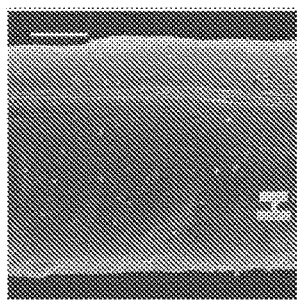
Figure 4C:
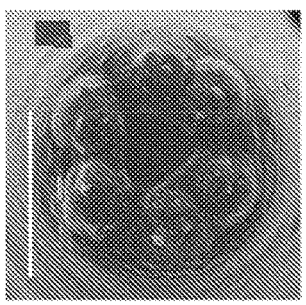
Figure 4G:
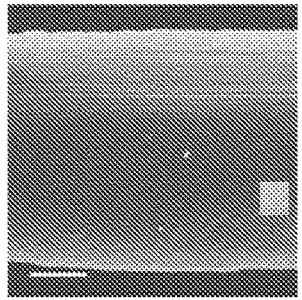
Figure 4B:
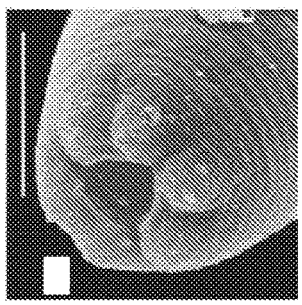
Figure 4F:
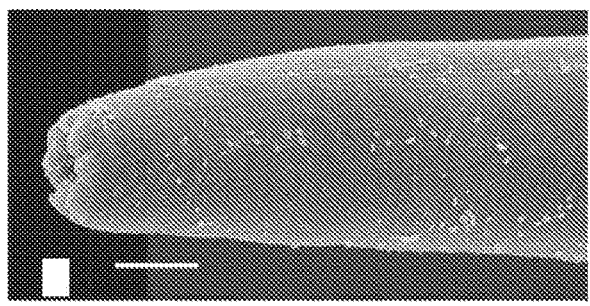
Figure 4A:
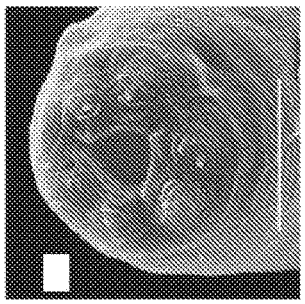
Figure 4E:
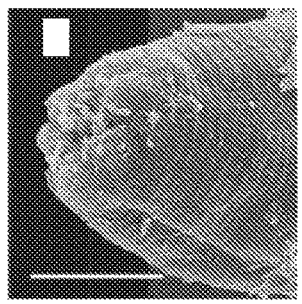

*P. papillosa* is morphologically and morphometrically close to *P. californica*. Body 1.2-1.9 mm long, robust, almost straight or slightly curved in the middle when relaxed by heat (FIG. 3H). Annules fine and less prominent under light microscope. Lateral field with six (SEM) prominent incisures. Anterior end bluntly rounded, lip region 16 (13-20) μm wide, continuous with body, six lips grouped in pairs (FIG. 4A-C). One labial papilla protruding anteriorly from each lip with a clearly demarcated inner labial dendrite emerging apically (FIG. 4B). Two less prominent outer cephalic papillae on dorsal lip pair and one each on subventral pairs. Mouth triangular (FIG. 4A-C) with slightly convex sides. Stoma 20 (16-25) μm long, 1.4 times as long as lip region diam., with distinct cheilostom, gymnostom, and stegostom with mean lengths of 6, 4 and 12 μm, respectively. Stegostom ending with well developed, rounded, isomorphic metarhabdions, each with three minute tubercles. Corpus cylindrical (FIG. 3E), 2.5 times as long as isthmus with slightly enlarged non-valvular metacorpus narrowing into isthmus and a pyriform basal bulb with finely-striated valvular apparatus. Nerve ring surrounding the isthmus, at 72% of the neck length. Deirids not prominent.

Figure 3D:
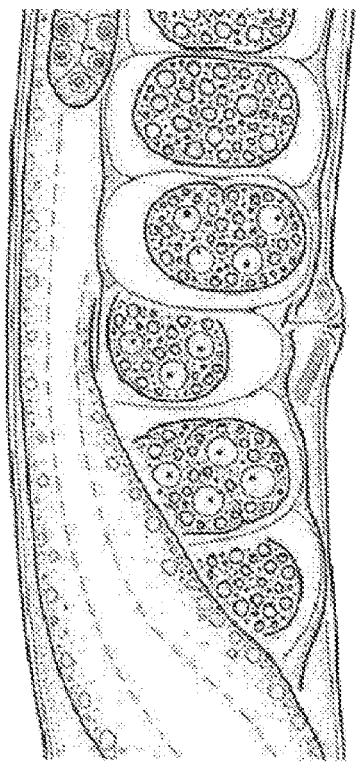
Figure 5C:
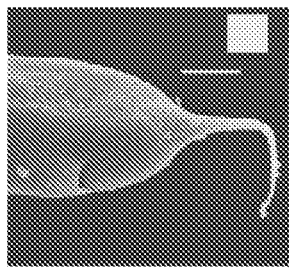
FIGS. 5A-F. SEM of *Phasmarhabditis papillosa* female (A-C) and male (D-F). Lateral field at midbody or vulval region (A); ventral view of the vulva and latero-ventral view of the posterior region showing the tail, anus, and posterior, prominent phasmids. Latero-ventral views of the male posterior region (D-F) showing the open peloderan tail, anus, and posterior, prominent phasmids, protruded spicules and nine pairs of caudal papillae.
Figure 5F:
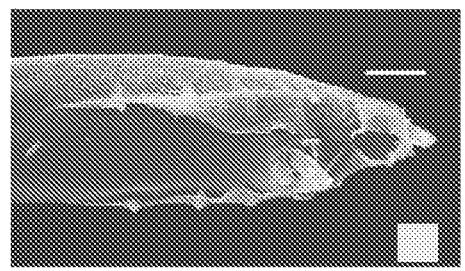
Figure 5B:
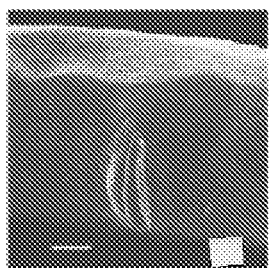
Figure 5E:
Figure 5A:
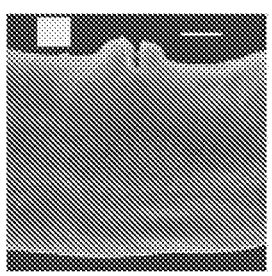
Figure 5D:
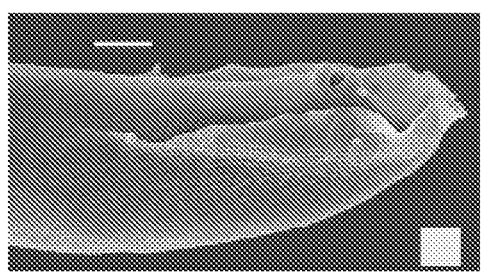
Figure 6:
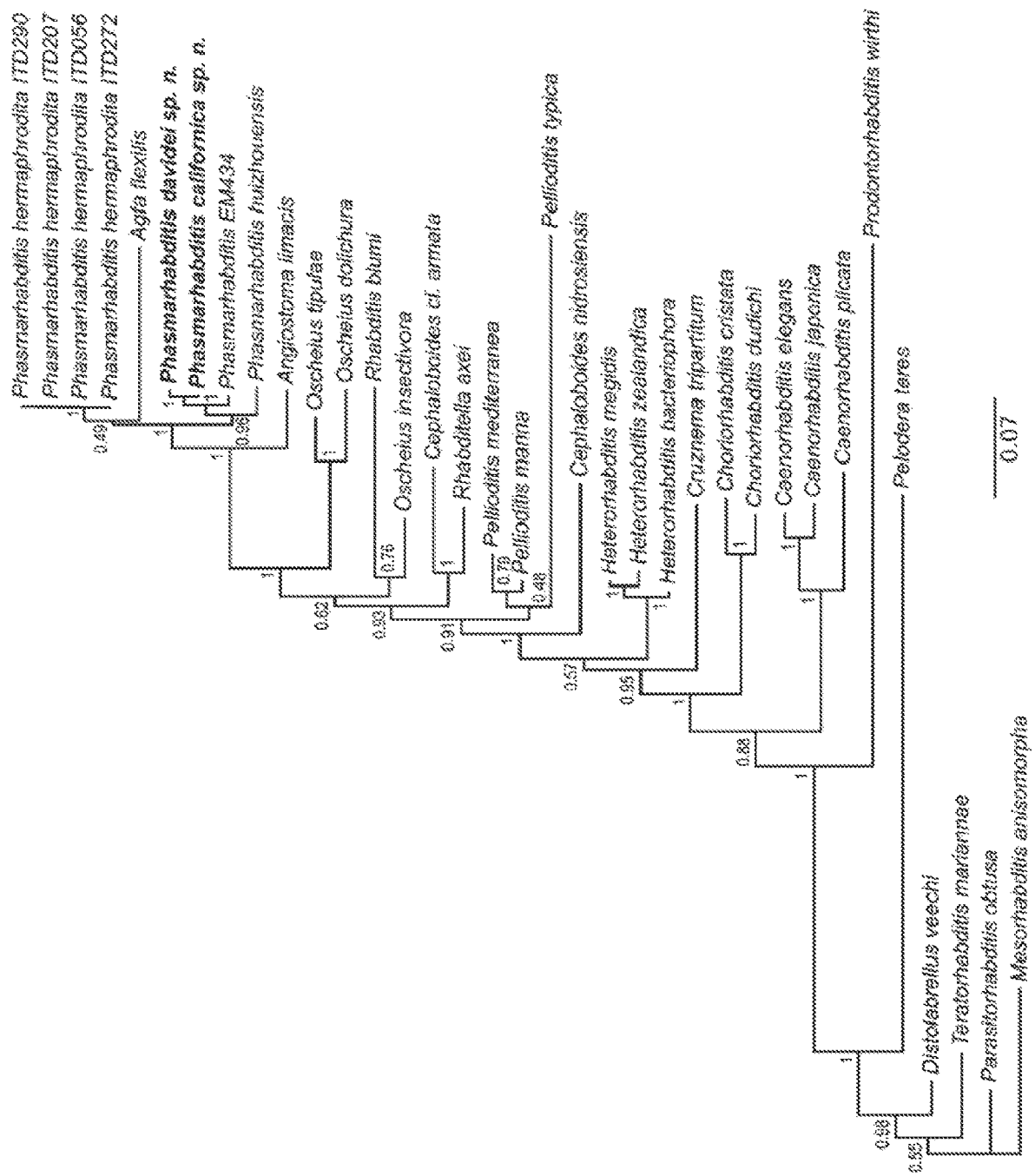
FIG. 6. Majority-rule consensus tree of the Bayesian phylogenetic analysis inferred from a secondary structure alignment of concatenated ribosomal DNA sequences including the nearly complete small subunit gene (SSU) and the D2-D3 expansion segments of the large subunit gene (LSU) rooted using *Mesorhabditis anisomorpha*. Branch lengths represent the mean posterior estimates of the expected number of substitutions per site.

Excretory pore when visible, very posterior, opening at middle or near base of terminal bulb. Reproductive system didelphic, amphidelphic, ovaries reflexed with tips sometimes reaching near or level of vulva (FIG. 3D). Anterior and posterior ovaries as measured from vulva to anterior/posterior flexure, occupying 25% anterior and posterior to the vulva. Spermatheca present and often filled with numerous sperm. Gonads of mature females often filled with round oocytes commonly hatching inside the body (FIG. 3D). Vulva a transverse slit halfway along body. Length of vagina variable, sometimes extending more than half the vulval body diam. Intestine ending in a rectum 0.9 (0.7-1.2) anal body diam. long with three cell bodies of associated sphincters (FIG. 3F). Anus an arcuate slit (FIG. 5C). Anal body diam. 37% of tail length. Phasmids prominent, position variable, located at 84 (72-95) % of the wider part of the cupula-shaped tail (FIGS. 3F, H and 5C). The wider part occupies almost half of the entire tail (FIGS. 3F and 5C).

Male (Table 2)

Adult males are cylindrical like the female with slightly ventrally arcuate-conical tail; body generally shorter and smaller than females but stoma, lip and pharyngeal regions similar (FIG. 3I). Copulatory apparatus consists of several structures (FIG. 3G, 5D-F): The spicules; gubernaculum; and the fan (=bursa), a lateral extension of the cuticle from the tail, holding nine bilateral pairs of sensory papillae (=rays) arranged as follows: three pairs pre-cloacal, one pair ad-cloacal, two pairs post-cloacal, and three pairs fairly close to the tail terminus. Ray formula 3/1+2+3. Bursa open, peloderan; spicules cephalated, paired and separate, 56 (47-67) μm long; with spatulate gubernaculum of 28 (22-37) μm long.

Locality and Habitat

Specimens (ITD510) for redescription were obtained from subcultures of nematodes that emerged from a cadaver of *D. reticulatum* that was collected from a garden center in San Diego, Calif., USA.

Diagnosis and Relationships

Morphologically, species are distinguished within this genus by morphometrics, absence or presence of males, bursa papillae, spicule size, and some female tail characters. In practice, species diagnostics is extremely difficult using only this classical approach, among others because males are very rare in most known species. *P. californica* and *P. papillosa* female measurements are very close and characterized by plasticity. These species, along with the others recently characterized or described will be difficult to separate only on the bases of morphometric characters, with the exception of *P. neopapillosa* (see Table 2) in having the longest and widest body (mean=2.2 mm, range 1.8-2.4 mm long; mean=141 μm, range 101-174 wide). Measurements of *P. neopapillosa* were made from specimens recovered directly from infested slugs, and they were approximately 20% bigger than *P. hermaphrodita*, also obtained from slug cadavers (Hooper et al., 1999). Measurements of our new species overlap with those of *P. hermaphrodita* grown in vitro.

However, there are a few morphological characters that are of use in distinguishing the species. *P. hermaphrodita* has a conical tail, sharply tapering towards the filiform terminus (FIG. 1 D, E of Hooper et al., 1999); *P. californica* has a short, conoid tail (mean=83, range=66-94 μm), that is constricted at one-third its length, appearing like a funnel (FIGS. 1D & 2E, F); and *P. papillosa* females have a longer tail (mean=106, range=73-130 μm) that is convex to dome-shaped spicate, with constriction halfway along its length (FIGS. 3F & 5C). In addition, *P. papillosa* has a longer isthmus (mean=43, range=37-49 μm) and a pyriform basal bulb, while *P. californica* has a slightly wider metacorpus, shorter isthmus (mean=59, range=45-63 μm) and a rounded-pyriform basal bulb.

Another distinguishing character is their mode of reproduction. *P. papillosa* is gonochoristic with numerous males in culture while *P. californica* is hermaphroditic. Females of *P. papillosa* hatched from isolated eggs and matured in vitro produce hundreds of infertile oocytes only. Other juveniles hatched in isolation switched to facultative diapause and became dauer larvae.

Species Diagnostics

*P. californica* is hermaphroditic, with rounded to pyriform basal bulb, and short, conoid tail, constricted at one-third its length. Not a single male among five strains.

*P. papillosa* is gonochoristic, female with convex to dome-shaped, spicate, long tail, constricted halfway along its length and pyriform basal bulb. Male frequent, ray formula 3/1+2+3.

Sequence Analysis and Molecular Phylogeny

D2-D3 sequence divergence was higher (5.23%) between *P. hermaphrodita* and *P. californica*, followed by *P. hermaphrodita* vs *P. papillosa* (4.8%), and *P. californica* vs *P. papillosa* (0.8%) (cf Table 2, Tandingan De Ley et al., 2014). Furthermore, the divergences of these three to *Phasmarhabditis* EM434 *hermaphrodita* range from 3.3-5.8%. As for the SSU dataset, greatest genetic distance was found between *P. hermaphrodita* vs. *P. papillosa* (3.1%), followed by *P. hermaphrodita* vs *P. californica* (2.7%), with the same least distance between *P. californica* and *P. papillosa* (0.7%). The only other sequenced species with male, *P. neopapillosa*, had 3.8% divergence from *P. papillosa*.

Figure 7A:
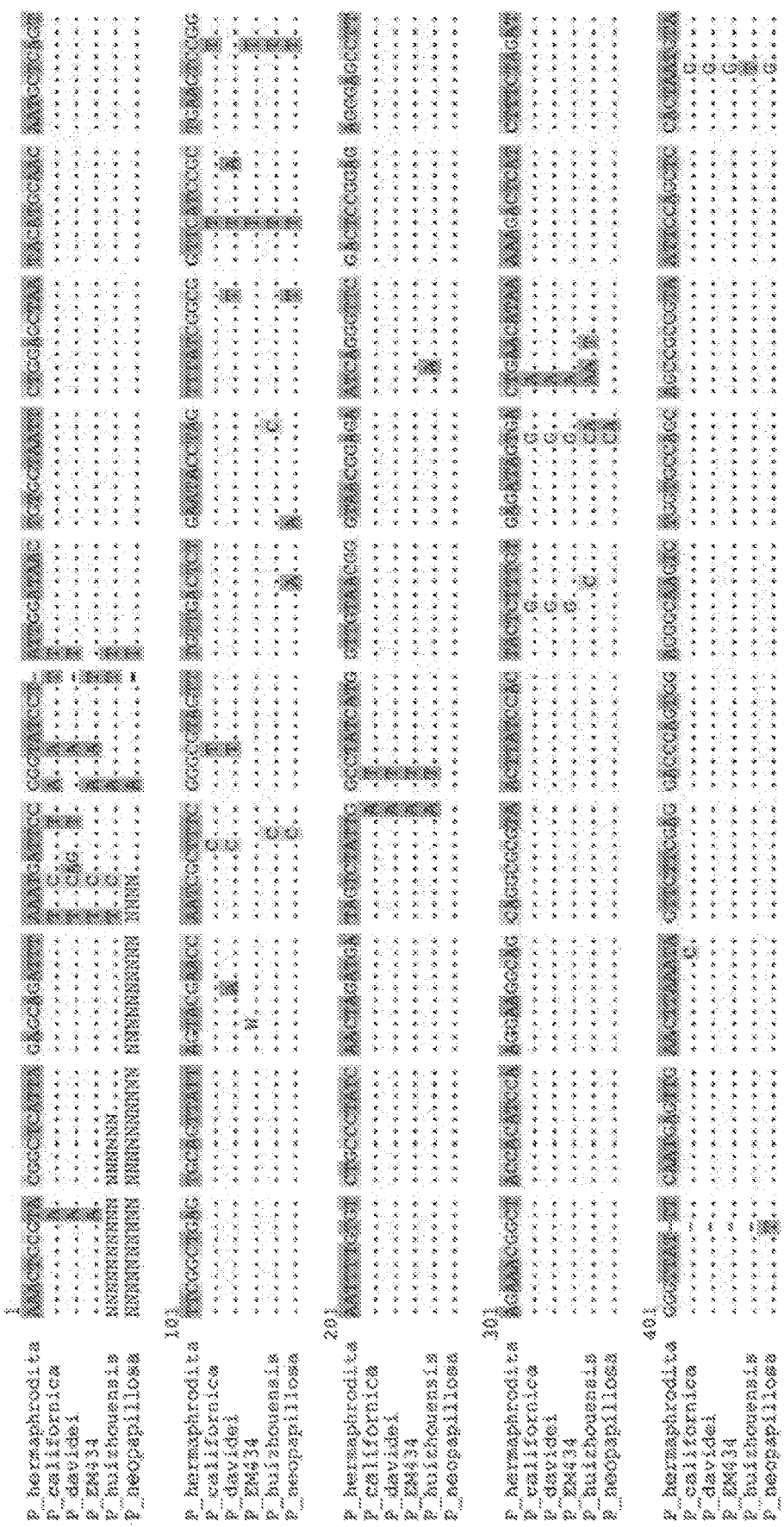
FIGS. 7A-B. Secondary structure-based multiple sequence alignment of ribosomal DNA sequences including the nearly-complete small subunit gene (SSU) and D2-D3 expansion segments of the large subunit gene (LSU) of *Phasmarhabditis* showing differences between considered species.
Figure 7A:
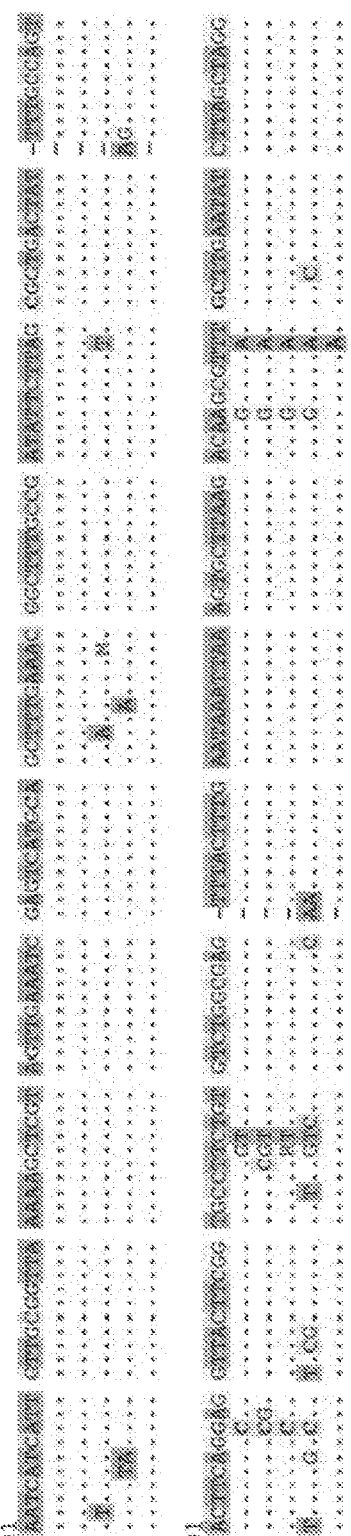
Figure 7B:
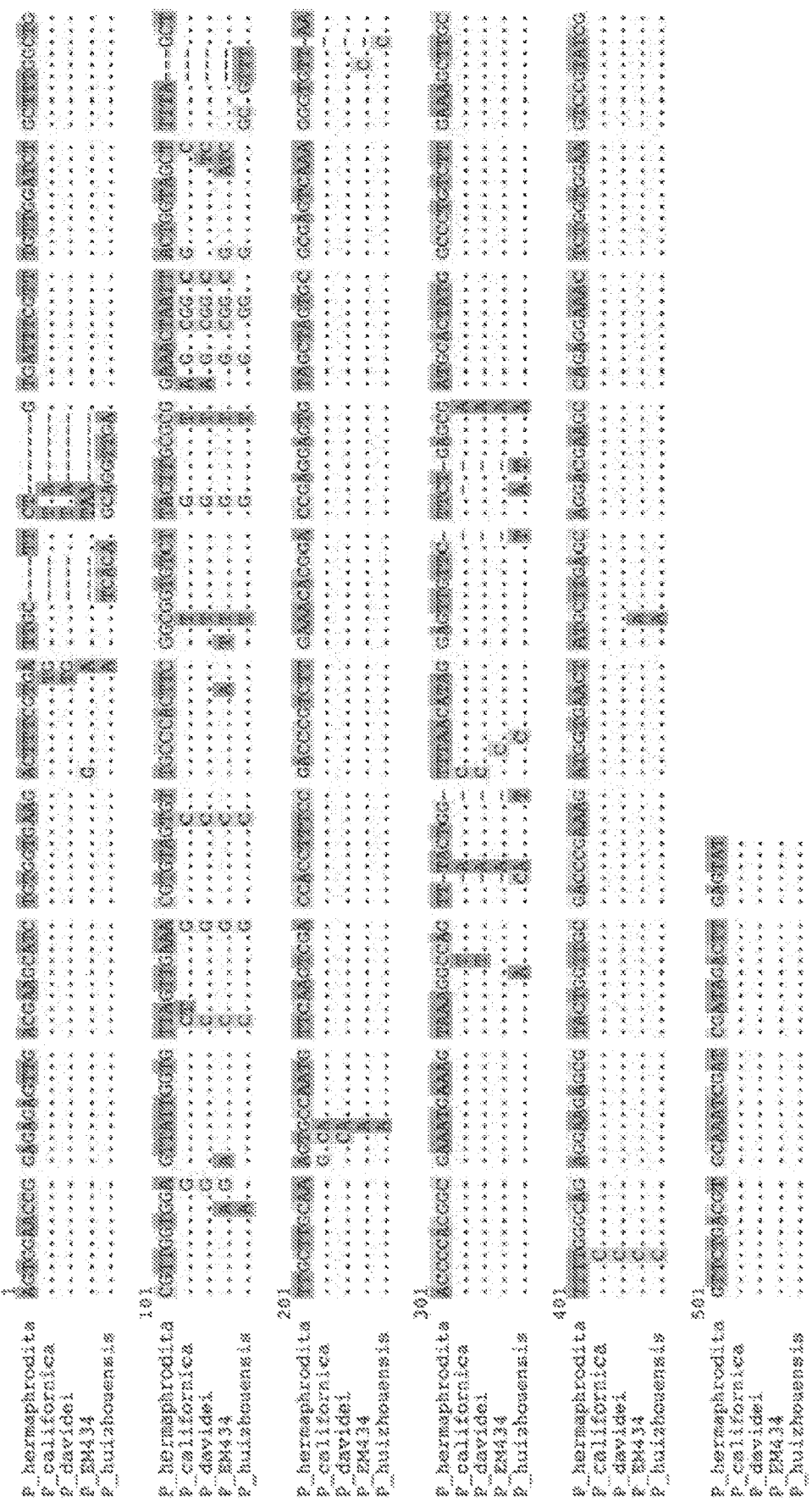

The 35-taxa, concatenated SSU and D2-D3 dataset contained 2334 nucleotide positions with 1725 and 609 nucleotides for the former and the latter, respectively. There were 20 (seven for SSU, 13 for LSU) unambiguous autapomorphies for *P. hermaphrodita*; eight (all SSU) for *P. papillosa*; while there were three (two with D2-D3 domains and one for SSU) for *P. californica* (FIG. 7a, b; Table 3).

TABLE 3

List of autapomorphies for three Californian *Phasmarhabditis* species based on the concatenated LSU and SSU rRNA sequences[1].

| Species | Gene, nucleotide position | Transition | Transversion |
| --- | --- | --- | --- |
| *P. californica* | LSU, 123 | | A -> T |
| | LSU, 211 | A -> G | |
| | SSU, 429 | T -> C | |
| *P. hermaphrodita* | SSU, 184 | T -> C | |
| | SSU, 679 | | A -> T |
| | SSU, 725 | | T -> A |
| | SSU, 786 | T -> C | |
| | SSU, 964 | | T -> A |
| | SSU, 1256 | | C -> A |
| | SSU, 1570 | T -> C | |
| | LSU, 122 | C -> T | |
| | LSU, 130 | G -> A | |
| | LSU, 138 | C -> T | |
| | LSU, 153 | T -> C | |
| | LSU, 162 | G -> A | |
| | LSU, 169 | T -> C | |
| | LSU, 183 | G -> A | |
| | LSU, 187 | G -> A | |
| | LSU, 188 | G -> A | |
| | LSU, 214 | A -> G | |
| | LSU, 334 | | A -> T |
| | LSU, 370 | G -> A | |
| | LSU, 404 | C -> T | |
| *P. papillosa* | SSU, 35 | G -> A | |
| | SSU, 36 | A -> G | |
| | SSU, 126 | G -> A | |
| | SSU, 189 | G -> A | |
| | SSU, 609 | A -> G | |
| | SSU, 625 | T -> C | |
| | SSU, 717 | T -> C | |
| | SSU, 718 | | A -> T |

[1]Total of 2334 positions containing 1725 (SSU) and 609 (LSU) nucleotide positions Phylogenetic analyses placed *P. papillosa* and the new species in a strongly-supported clade comprised of *Phasmarhabditis* isolate EM434, *P. huizhouensis*, *P. hermaphrodita*, and gastropod-parasitic nematode taxa *Agfa flexilis* and *Angiostoma limacis*. *P. hermaphrodita* is sister to *A. flexilis* and together form a sister clade to the other four *Phasmarhabditis* species with *Angiostoma limacis* as the basal taxon.

This result is consistent with the tree topology as inferred from nearly-complete SSU, placing gastropod-parasitic nematodes from three morphologically divergent families (Agfidae, Angiostomatidae and Rhabditidae) in monophyletic Clade V (Ross et al., 2010).

Discussion

*Phasmarhabditis* species are known to be morphologically conservative and therefore, accurate and fast diagnostics within this group will only be possible with molecular sequence-based approach. Kanzaki et al. (2012) introduced the concept of "reverse taxonomy" to primarily link the molecular operational taxonomic unit (MOTU) or DNA sequences with morphological archives, and then identify and/or describe them at genus/species level. Similarly, we have routinely used a combined Video Capture and Editing (VCE)-PCR approach, archiving morphology through videos and generating D2-D3 sequences, or molecular barcodes, for all nematode stages and specimens that are either un-culturable, or for which cultures are not available (De Ley et al, 2005; De Ley and Bert, 2002); and doing targeted morphological/morphometrical analysis at a later time. This is particularly important for juveniles and dauers, but also for most adults of Rhabditida. *Phasmarhabditis* is no exception. Additional targeted surveys in other parts of the United States may very well recover these and/or new species. For instance, *Phasmarhabditis* EM434 was recovered from earthworms in The Bronx, N.Y.; and possibly the same species (based on similar partial 28S rDNA sequences) baited by *Galleria mellonella* L. grubs in Utah (http://jur.byu.edu/?p=3491); as well as earthworms (*Lumbricus terrestris* L.) at the University of Illinois at Urbana-Champaign, Ill. (Zaborski et al., 2001).

Finding stable taxonomic characters is a challenge for this group, it is a very slow process and often characters and taxa are missed. With additional surveys, continuous expansion of existing databases (e.g. GenBank) and availability of molecular barcodes for nematodes, diagnostics and species discovery will be faster and more efficient.

In conclusion, there are currently three *Phasmarhabditis* species in California: *P hermaphrodita*, *P. papillosa* and one new to science, *P. californica*.

*P. hermaphrodita* was recovered from invasive slug taxa *D. reticulatum*, *D. laeve*, and *L. valentiana*; *P. papillosa* from a single specimen of *D. reticulatum*; while the new species *P. californica* from four invasive slug taxa *A. hortensis* agg., *D. laeve*, *D. reticulatum*, and *L. valentiana* from nurseries and garden centers in California. This new species along with their closely-related species, may be morphologically conservative, however, some characters are useful for species diagnostics: (a) the shape and length of the female tail and isthmus length; (b) genetic divergence; (c) difference in reproductive strategies (hermaphroditic vs gonochoristic); and (d) presence of unambiguous autapomorphies that support validity of their species status based on phylogenetic species concept sensu Adams (1998, 2001).

Example 2

Trial 1
*Phasmarhabditis hermaphrodita* (Isolate ITD290) Versus the Pest Slug *Lehmannia Valentiana* (Trial 1a)

*Lehmannia valentiana* is a serious pest of ornamental plant production throughout the US and in many other parts of the world. An experiment was designed with three treatments (no infective juveniles [IJs]; recommended rate of 30 IJs/cm2 soil, and five times the recommended rate at 150 Us/m2) in three replicates. The recommended rate in the bioassays is based on the recommended application rates for Nemaslug®. The autoclaved soil used in the arena is composed of 75% SunGro Sunshine No. 4 mix and 25% UCR Agricultural Operations mix. Non-airtight disposable plastic containers were used to ensure air circulation within the arena.

Nematode inoculum (ITD290, isolated from *L. valentiana*) was built up on freshly killed slugs and incubated at 17° C. (Wilson, 2012). IJs were collected starting from 10 days after inoculation and the nematodes inoculated on the sterile soil surface in assay plates before introducing pre-weighed slugs. Mostly mature *L. valentiana* specimens were weighed and assigned to different size classes. Similar size classes were assigned to replications, and experimental units were randomized among treatments. Five slugs were provided per treatment/arena. Mortality was recorded for 18 days. Surviving slugs were transferred to individual plates and feeding inhibition was determined based on the amount of food (pre-weighed carrot) consumed.

Figure 8:
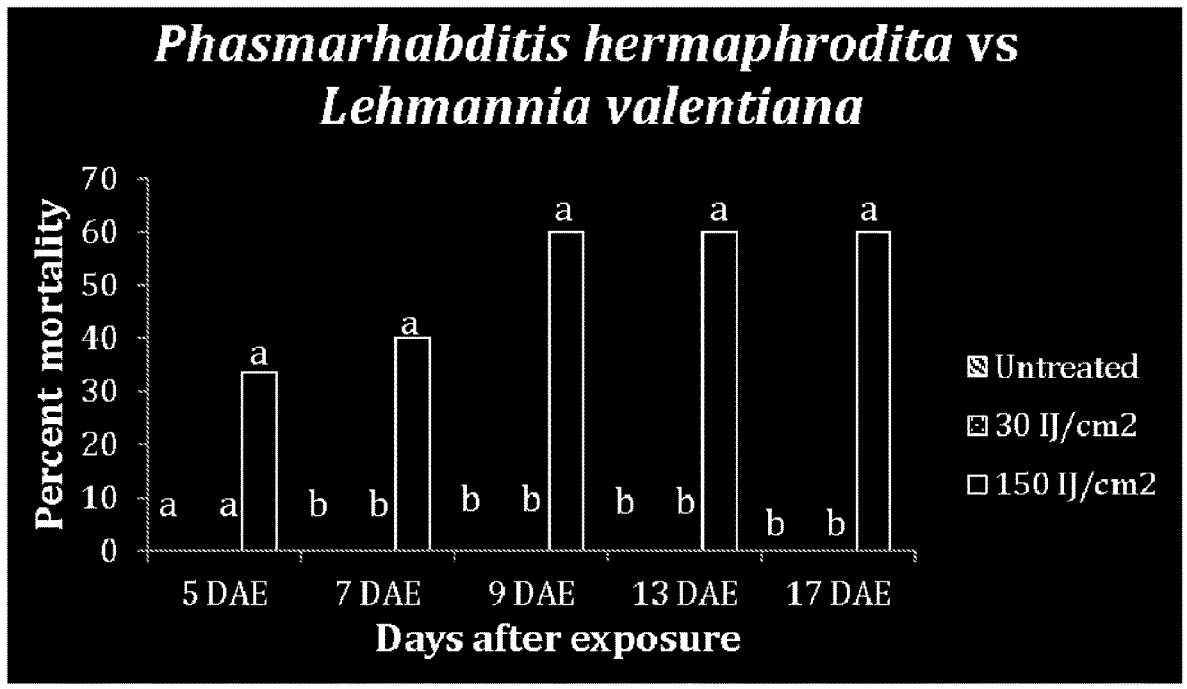
FIG. 8. Percent mortality of *Lehmannia valentiana* exposed to 30 IJ and 150 IJ of *Phasmarhabditis hermaphrodita* per $cm^2$.

Three days after exposure, *L. valentiana* at the higher rate of 150 IJ/cm$^2$ exhibited swelling of the mantle, that progressed to constriction of the area behind the mantle, exposure of the shell cavity, extrusion of the vestigial shell, and rupture of the integument. At five days after exposure (DAE), slugs are dead or in varying degrees of symptom development with hundreds of nematodes swarming either in the "pool" of the shell cavity or over the cadaver. At 9 DAE, mortality (60%) was significantly ($p<0.01$; FIG. 8) greater at the higher rate of 150 IJ/cm$^2$ compared to the other rate and control. However, at the lower recommended rate of 30 IJ/cm$^2$ the slugs also showed milder symptoms of infection. Slug mortality remained at the same 60% level 17 DAE. This constitutes the first report of *L. valentiana* mortality due to *Phasmarhabditis hermaphrodita* (cf Tandingan De Ley et al., 2014; 2016).

*Phasmarhabditis hermaphrodita* (ITD290) Versus *Lissachatina Fulica* (=*Achatina fulica*, Trial 1b)

A parallel experiment was set up to test the isolate's efficacy on Giant African land snail (*Lissachatina fulica*) neonates. *L. fulica* is listed as one of the top 100 and most damaging invasive species in the world (Lowe et al., 2004), and is known from and problematic in North America (Lach and Cowie, 1999; Cowie, 2001). Its pest status is compounded by the fact that it is also a vector of the potentially fatal meningoencephalitis in humans (Wang et al., 2012). A USDA approved colony (permit number P526P-14-01916) of this species is located in the restricted access Biosecurity Level 2 Quarantine Facility at UC Riverside, and this is where the trials with the species were conducted. Although not yet established as a pest outside of Florida and Hawaii, this species represents a serious threat to Specialty Crops in the US and is being intercepted at air and sea ports. The same treatment arenas described above were used, with eight *L. fulica* neonates per treatment. Mortality was also recorded at 5, 7, 9, 13 and 17 DAE.

Figure 9:
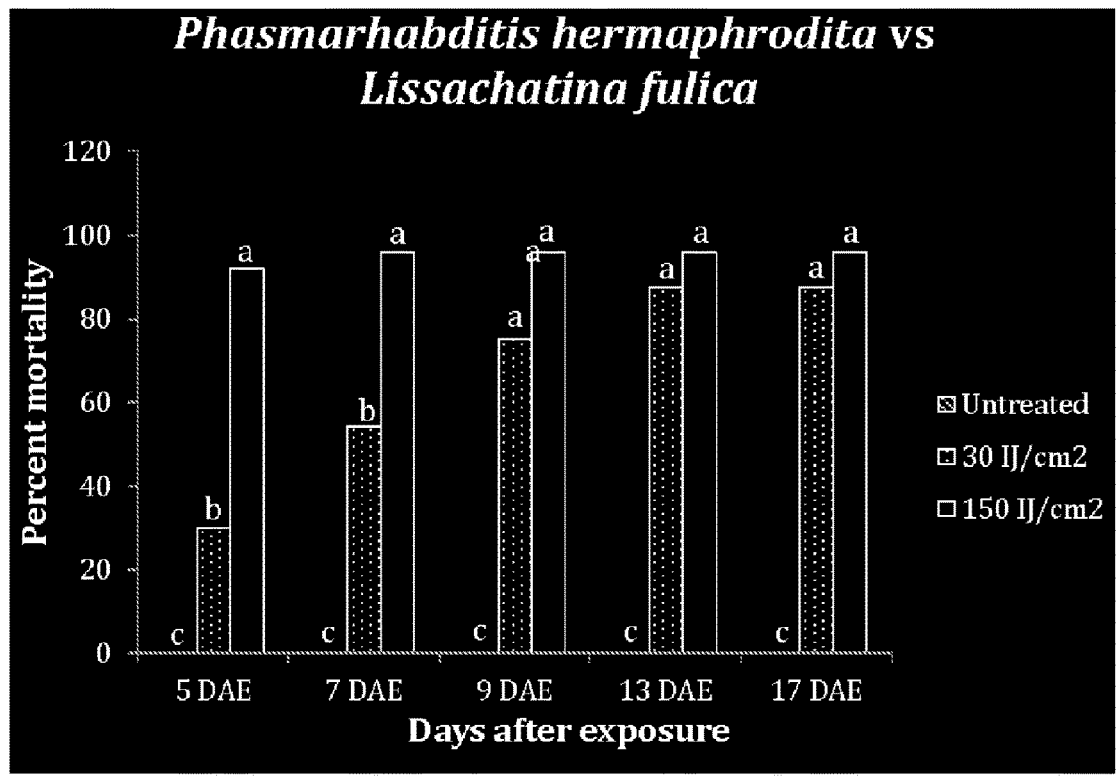
FIG. 9. Percent mortality of *Lissachatina fulica* exposed to 30 IJ and 150 IJ of *Phasmarhabditis hermaphrodita* per $cm^2$.

Percent mortality was highly significant between treatments. Starting from 5DAE ($p<0.02$) until the termination of the assay ($p<0.01$), with 92% mortality recorded at the higher concentration of 150 IJ/cm$^2$, increasing to almost 100% 9 DAE until 17 DAE (FIG. 9). Starting at 9 DAE, 30 and 150 IJ/cm$^2$ were equally effective.

This is the first proof of *L. fulica* mortality caused by exposure to *P. hermaphrodita*. Using the same rates of Nemaslug® did not cause mortality in 12-week old *L. fulica* (Williams and Rae, 2015). They also found that as early as 3 DAE, the snails encapsulated and killed invading *P. hermaphrodita*, so further studies on susceptibility at different stages or size classes will be useful as we evaluate the biological control potential of the US strain of the species and isolates of other *Phasmarhabditis* against such damaging invasive gastropods.

Trial 2
*Phasmarhabditis hermaphrodita* (Isolate ITD290) Versus *Lehmannia valentiana, Limacus flavus, Lissachatina fulica* and *Cornu aspersum*

Xenic cultures of isolate ITD290 of *P. hermaphrodita* were assayed against *Lehmannia valentiana* (Valencia slug), *Limacus flavus* (Tawny garden slug), *Cornu aspersum* (Brown garden snail), and *Achatina fulica* (Giant African land snail), corresponding to four infectivity tests. Inoculum of *P. hermaphrodita* was prepared using a modified White trap (Wilson, 2012). Chunks of agar with adult actively growing female nematodes were aseptically introduced on freshly killed slugs and plates were incubated at 17° C. IJs (=Dauers) were collected from three-week old set up and inoculum quantified and standardized just prior to its use.

Figure 10:
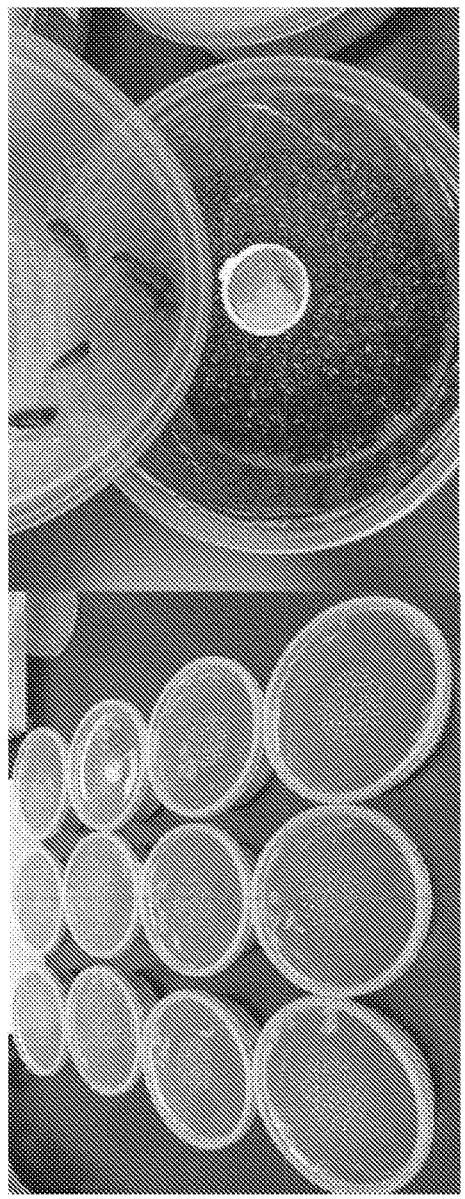
FIG. 10. Plastic arena (left) for infectivity tests on *Phasmarhabditis hermaphrodita* against gastropods. Gastropods fed with lettuce leaf discs (right) two weeks after dauer exposure.

The autoclaved soil used in the arena is composed of 75% SunGro Sunshine No. 4 mix and 25% UCR Agricultural Operations mix. There were three treatments (untreated, the recommended rate of 30 IJs/cm$^2$ and 150 IJs/cm$^2$) in four replicate plastic non-airtight disposable containers as the arena (FIG. 10). These containers and lids were used to maintain a balance between air circulation in the arena, thus preventing volatile-induced slug mortality; and sufficient moisture for slug survival. Copper strip tapes were provided along the wall of the container to prevent test specimens from moving up to the lid. Despite the strips, slugs still moved and stayed most of the time on the lid, trailing nematodes with them.

Test gastropods were weighed and assigned to different size classes. Similar size classes were assigned to replications, and experimental units were randomized among treatments. There were ten slugs or snails per treatment arena except for *L. flavus* which contained eight. Mortality was noted for three weeks.

a). *Phasmarhabditis hermaphrodita* (ITD290) Versus *Lehmannia valentiana*

Figure 11:
FIG. 11. *Lehmannia valentiana* with typical swollen mantle (left), and a ruptured integument just behind the cavity (right) three days after exposure to *Phasmarhabditis hermaphrodita* (ITD290).
Figure 12:
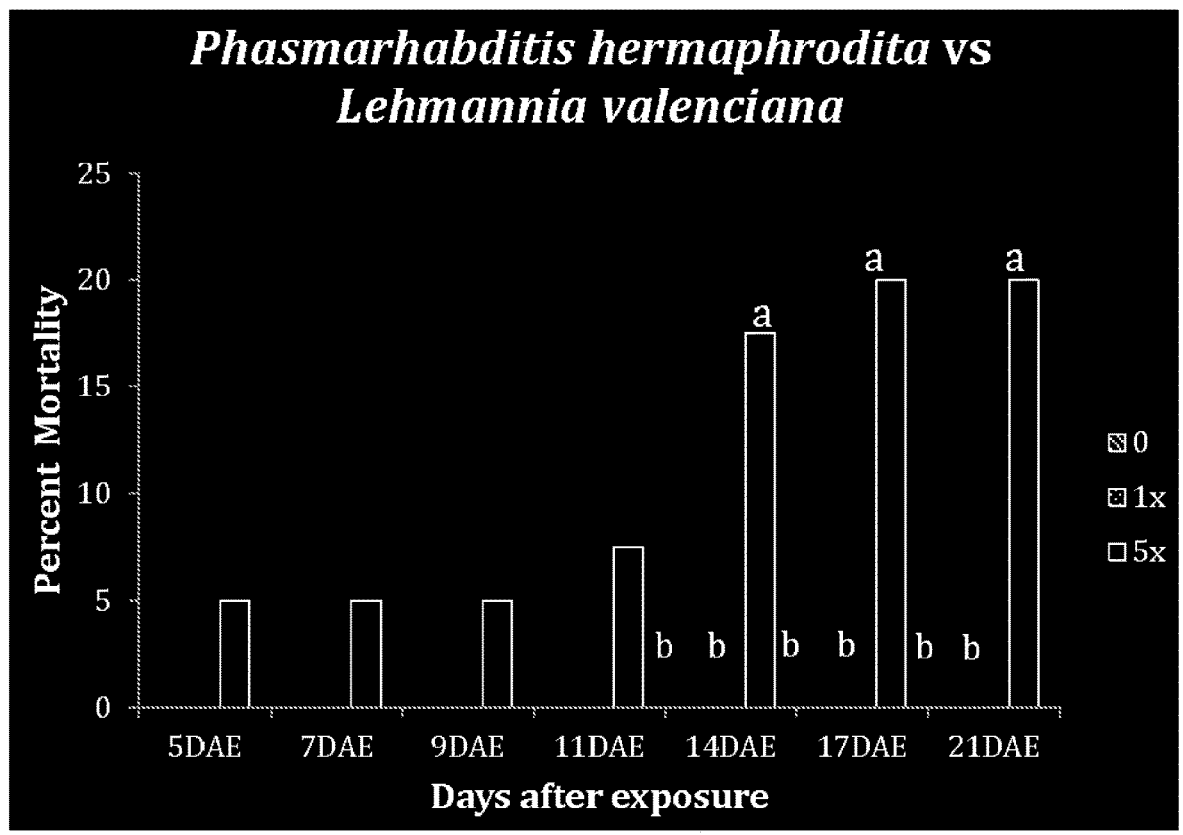
FIG. 12. Percent mortality of *Lehmannia valentiana* exposed to 30 IJ (1×) and 150 IJs (5×) per $cm^2$ of *Phasmarhabditis hermaphrodita* (ITD290).

As with trials (see above), three days after exposure to nematodes, *L. valentiana* at the higher rate of 150 IJ/cm$^2$ exhibited swelling of the mantle, that progressed to constriction of the area behind the mantle, exposure of the shell cavity, rupture of the integument and extrusion of the vestigial shell (FIG. 11). At 5 DAE, slugs were dead or in varying degrees of symptom development with hundreds of nematodes swarming either in the "pool" of the shell cavity or over the cadaver. From 14-21 DAE, treatment had a significant effect on slug mortality (p<0.01-0.001), with the dose of 150 IJ/cm$^2$ resulting in significantly higher mortality than 30 IJ/cm$^2$ (FIG. 12).

b). *Phasmarhabditis hermaphrodita* (ITD290) Versus *Limacus flavus*

Figure 13:
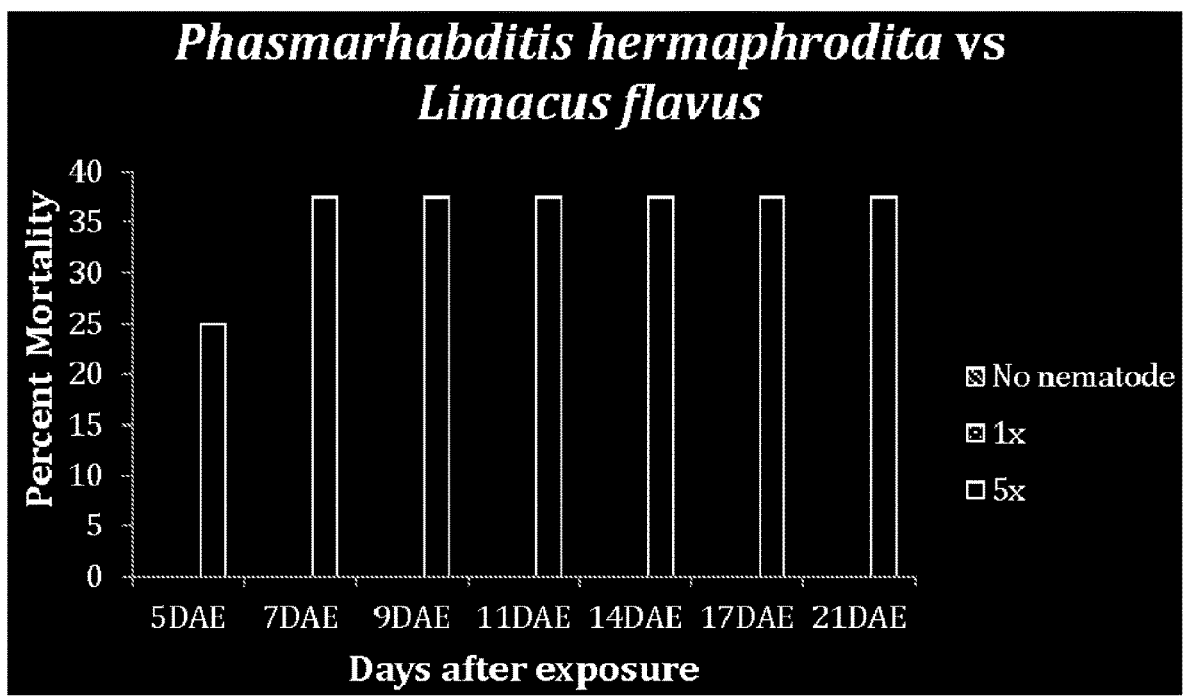
FIG. 13. Percent mortality of *Limacus flavus* exposed to 30 IJ (1×) and 150 IJs (5×) per $cm^2$ of *Phasmarhabditis hermaphrodita* (ITD290).

This is the first trial on the urban pest slug *L. flavus*, with isolate ITD290 of *P. hermaphrodita* but no statistically significant mortality was observed (FIG. 13). However, nematode exposure caused 37.5% mortality on smaller specimens of *L. flavus* (in only one replicate). The symptom development is very similar to *L. valentiana*, leading to death 4 DAE. This is the first record of *Phasmarhabditis hermaphrodita* causing mortality and infecting *L. flavus*. Further tests will be performed to determine whether nematode susceptibility of this slug is size- and species-dependent.

c) *Phasmarhabditis hermaphrodita* (ITD290) Versus *Cornu aspersum*.

Figure 14:
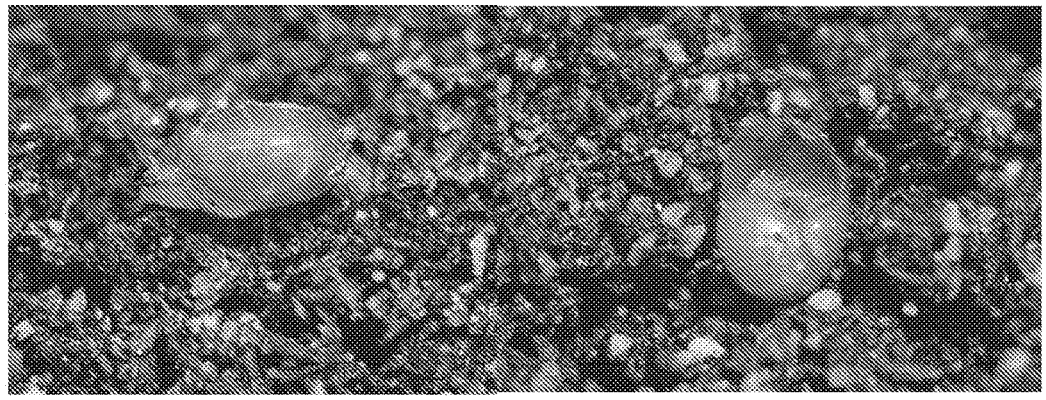
FIG. 14. Healthy (left) and *Phasmarhabditis hermaphrodita*-infected *Cornu aspersum* (right), showing a pool of nematodes on its foot. Photos taken one week after dauer exposure.
Figure 15:
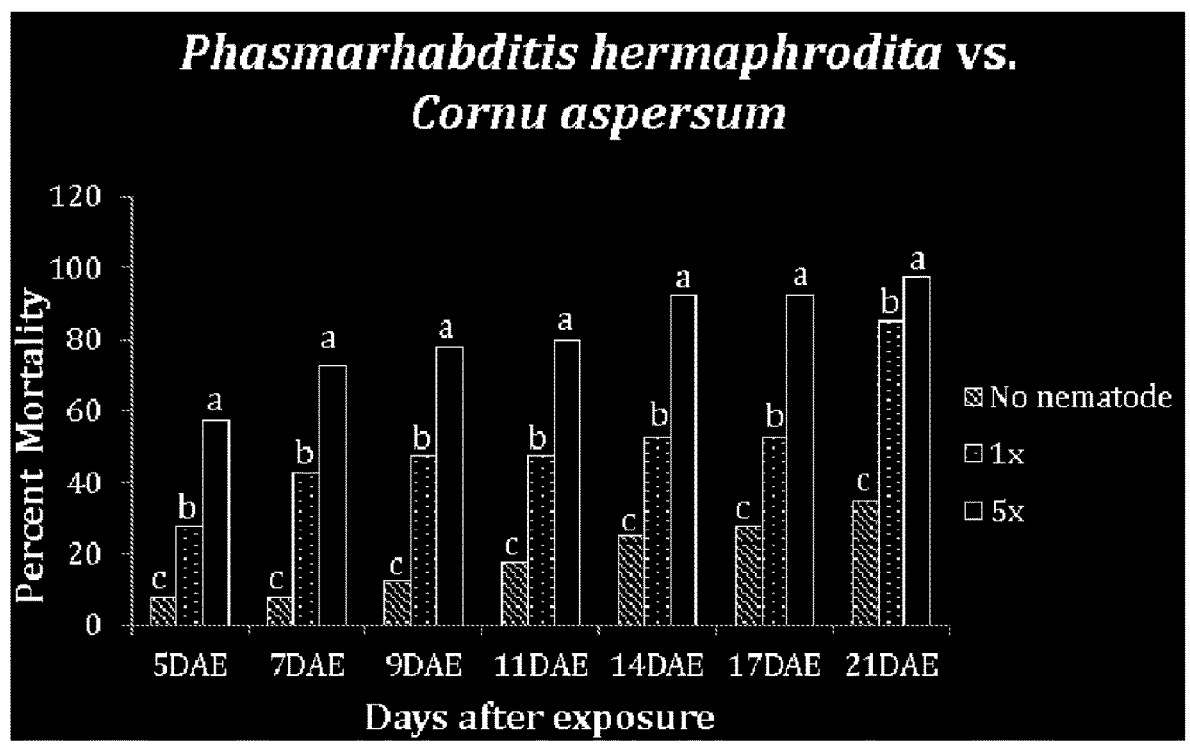
FIG. 15. Percent mortality of *Cornu aspersum* exposed to 30 IJ (1×) and 150 IJ (5×) per $cm^2$ of *Phasmarhabditis hermaphrodita*.

*Cornu aspersum* (also known as *Helix aspersa*) is a quarantine snail species and one of the most damaging pests in horticultural production throughout the world. This first assay with this snail species revealed susceptibility of young *C. aspersum* to *P. hermaphrodita*, even at the lower recommended dose of 30 IJs/cm.$^2$ Snails began moving slowly, and exposing foot muscles retracted towards the right side of the shell and oftentimes covered with numerous developing nematodes (FIG. 14). Snails were found dead on two application rates at 2 DAE. Starting at 5 DAE, nematode treatment caused significant (p<0.01) snail mortality with 58% mortality at 150 IJs/cm$^2$, and infectivity increased with time, reaching over 90% at 14 DAE (FIG. 15).

d) *Phasmarhabditis hermaphrodita* (ITD290) Versus *Lissachatina fulica*.

Figure 16:
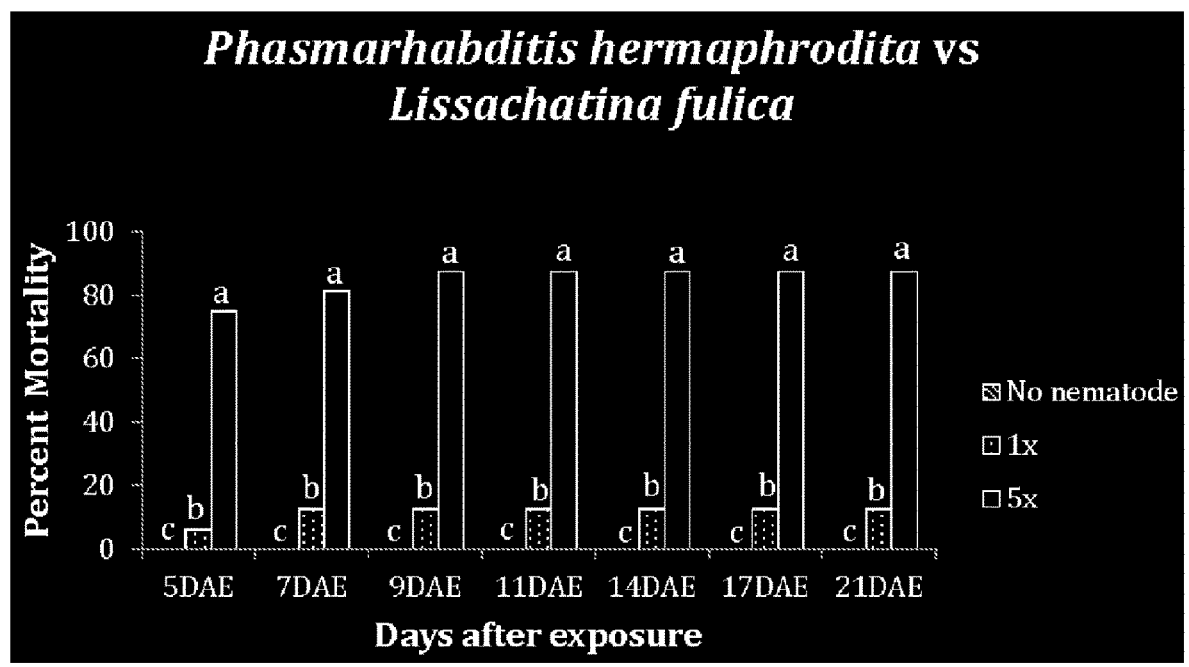
FIG. 16. Percent mortality of *Lissachatina fulica* exposed to 30 IJ (1×) and 150 IJ (5×) per $cm^2$ of *Phasmarhabditis hermaphrodita* ITD290.

This is the second assay involving neonate *Lissachatina fulica*. The first assay (see above) showed significant mortality of 75-100% even at the recommended rate of 30 IJ (1x) per cm$^2$ (FIG. 9). With this second trial, mortality was also highly (p<0.0001) affected by nematode application. Mortality was rate dependent, with the highest mortality at the higher concentration of 150 IJ per cm$^2$, increasing to almost 100% 9 DAE (FIG. 16). The lower, recommended rate only caused 12.5% mortality after three weeks of exposure. Nevertheless, this is the 2$^{nd}$ assay that demonstrates mortality of *L. fulica* after *P. hermaphrodita* application. In a recent study, the same rates of commercial product Nemaslug® did not cause mortality in 12-week old *L. fulica* (Williams and Rae, 2015). They also found that as early as 3 DAE, the snails encapsulated and killed invading *P. hermaphrodita*. This *P. hermaphrodita* isolate as well as the other two species of *Phasmarhabditis* may be used against different stages or size classes to control this invasive species.

Trial 3 a). *Phasmarhabditis hermaphrodita* (Isolate ITD272) Versus *Deroceras reticulatum*

Figure 17:
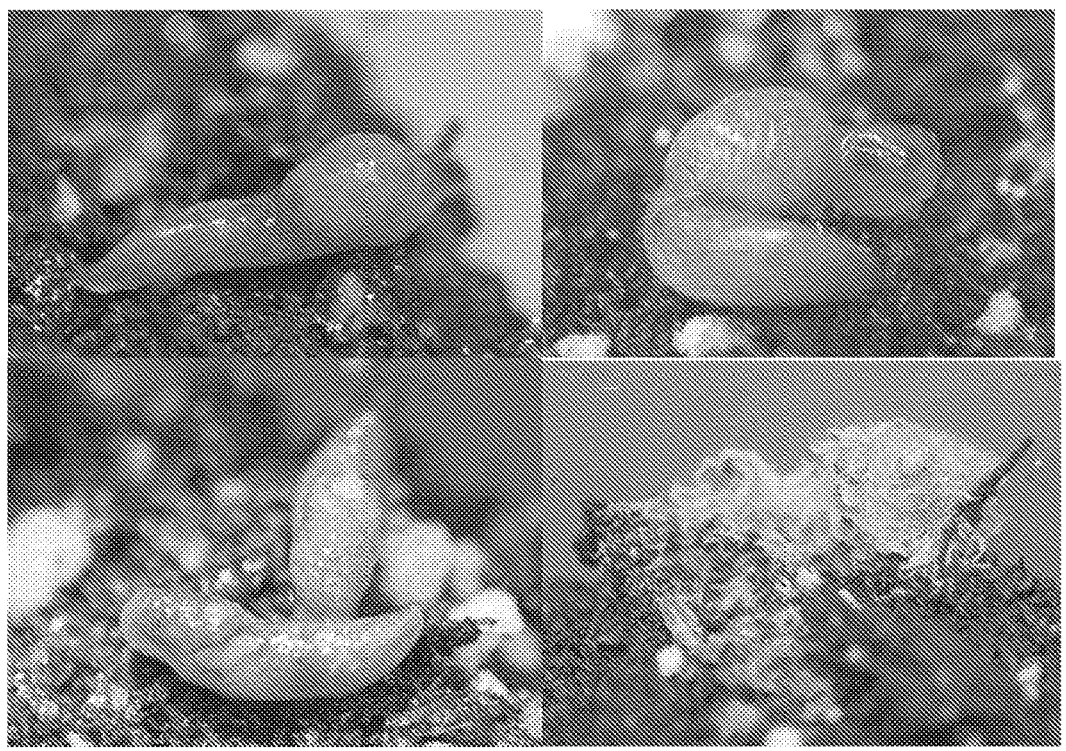
FIG. 17. *Deroceras reticulatum* with typical swollen mantle (top left), constriction behind the mantle (top right), exposed cavities and a ruptured integument (lower left) and developing nematodes on the cadaver. Photographs of different specimens taken 3-4 days after exposure to *Phasmarhabditis hermaphrodita* (ITD272)
Figure 18:
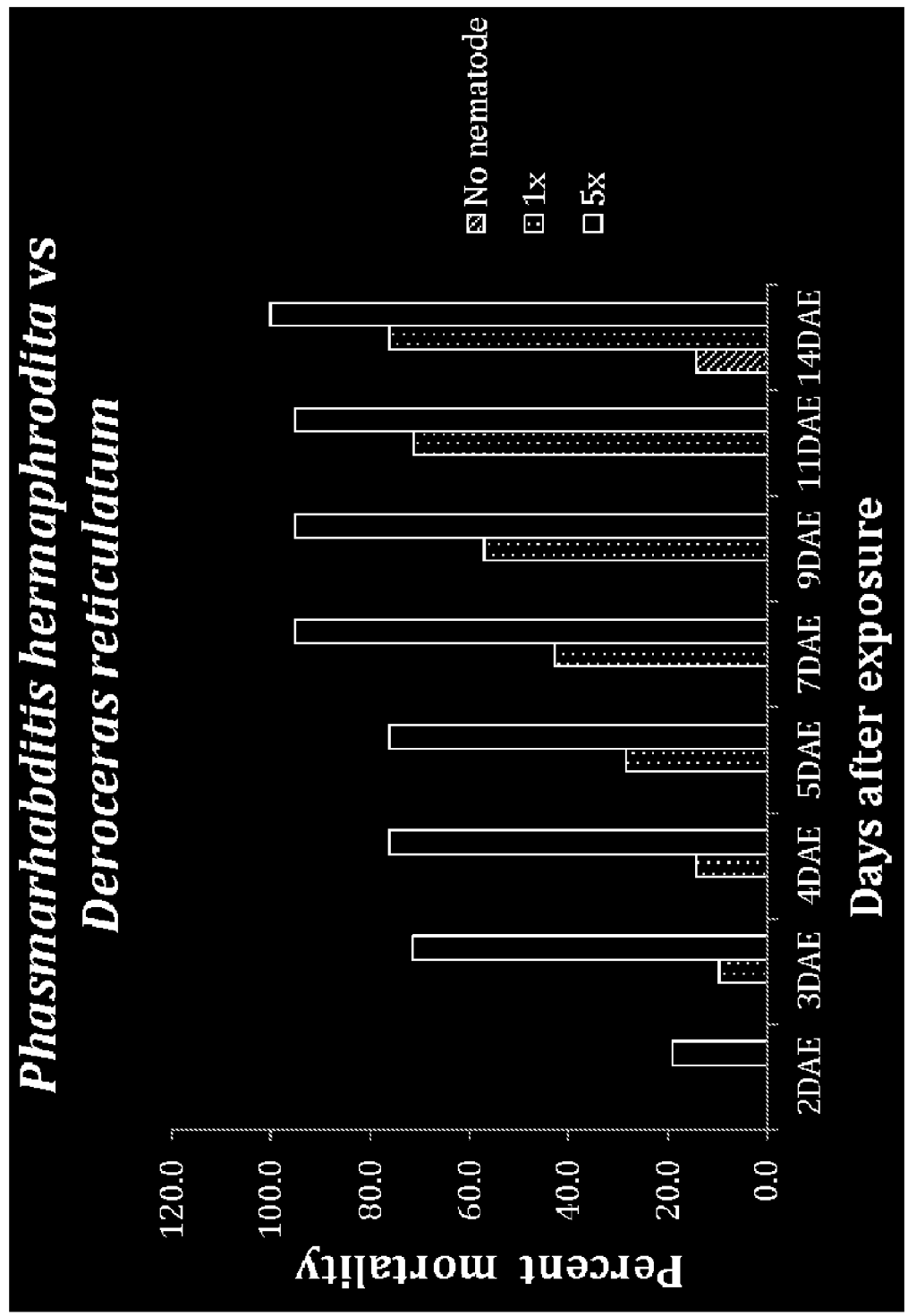
FIG. 18. Percent mortality of *Deroceras reticulatum* exposed to 30 IJ (1×) and 150 IJ (5×) per $cm^2$ of *Phasmarhabditis hermaphrodita* ITD272.

*Deroceras reticulatum* is widely regarded amongst scientists and farmers as the most damaging slug species in the world including North America. Symptom development on *D. reticulatum* is very similar to *L. valentiana*, with characteristic swelling of the mantle, girdling behind the mantle, exposure of the cavity with numerous developing nematodes, and nematodes eventually decomposing the cadaver leaving only the vestigial shell (FIG. 17). *D. reticulatum* is highly susceptible to the nematode as mortality was observed at 150 IJ/cm$^2$ as early as 2DAE (FIG. 18). At this higher rate, mortality increased to 76% at 150 IJ/cm$^2$ 5DAE, 95.2% at 7DAE (complete control in two of three replicates) and complete control 14DAE. At the lower rate of 30 IJ/cm$^2$, mortality was 57% at 9DAE and 76% 14DAE.

SUMMARY

The above assays demonstrated that the pest gastropods *C. aspersum*, *D. reticulatum*, *L. flavus*, *L. valentiana* and *L. fulica* are suitable hosts and exhibited varying degrees of susceptibility to the US isolate of *P. hermaphrodita*. *L. valentiana*, *L. flavus* and *L. fulica* are new host records for *P. hermaphrodita*. Biological control effectivity of *P. hermaphrodita* appears to be dependent on the rates of application and species of gastropods. In the present studies, *P. hermaphrodita* is most effective when applied at 150 IJ/cm$^2$ (about 1,000 IJ/gastropod) against *C. aspersum*, *D. reticulatum* and *L. valentiana* and *L. fulica*. However, rates between 30 and 150 IJ/cm$^2$ may also provide comparative mortality. *D. reticulatum* is highly susceptible to *P. hermaphrodita*, with complete control at 14 DAE.

REFERENCES

Adams, *Journal of Nematology*, 30:1 (1998).
Adams, *Journal of Nematology*, 33:153 (2001).
Andrássy, *A taxonomic review of the suborder Rhabditina (Nematoda: Secernentia)*. Paris, France, ORSTOM (1983).
Andrássy, *Free-living nematodes of Hungary. Vol. III*. Budapest: Hungarian Natural History Museum, Systematic Zoology Research Group of the Hungarian Academy of Sciences. 608 pp (2009).
Azzam, *Journal of the Egyptian German Society of Zoology*, 42:79 (2003).
Baird, *Nematology*, 3:373 (2003).
Chilton, *Molecular and Cellular Probe*, 17:33 (2003).
Cowie, *International Journal of Pest Management* 47, 23 (2001).
De Grisse, *Mededelingen Rijksfakulteit Landbouwwetenschappen Gent*, 34:351 (1969).
De Ley and Bert, *Journal of Nematology*, 34:269 (2002).
De Ley, *Nematologica*, 41:153 (1995).
De Ley, *Philosophical Transactions of the Royal Society of London. B, Biological Science*, 360:1945 (2005).
Ellis, *Nucleic Acids Research*, 14:2345 (1986).
France and Gerding, *Journal of Nematology*, 32:430 (2000).
Genena, *Archives of Phytopathology and Plant Protection*, 44:340 (2011).
Gowri-Shankar and Jow, PHASE: a software package for Phylogenetics and Sequence Evolution. University of Manchester, UK. (2006).
Grewal, *Journal of Nematology*, 35:146 (2002).
Gutell and Fox, *Nucleic Acids Research*, 16:r175 (1988).
Higgs, *Quarterly Review in Biophysics*, 33:199 (2000).
Hooper, *Nematology*, 1:173 (1999).
Huang, Morphology and molecular phylogeny of *Phasmarhabditis huizhouensis* sp. nov. (Nematoda: Rhabditidae), a robust rhabditid nematode from Guangdong Province, China. Unpublished. http://www.ncbi.nlm.nih.gov/nuccore/KP017252 (2015).
Kanzaki, *PLoS ONE*, 7(8): e43865. doi:10.1371/journal.pone.0043865 (2012).
Karimi, *Journal of Entomological Society of Iran*, 22:77 (2012).
Lach and Cowie, *Bishop Museum Occasional Papers* 58, 66 (1999).
Lowe, *The Invasive Species Specialist Group* www.issg.org/booklet.pdf (2004).

Miller, "Creating the CIPRES Science Gateway for inference of large phylogenetic trees" in Proceedings of the Gateway Computing Environments Workshop (GCE), 14 Nov. 2010, New Orleans, La. pp 1-8 (2010).
Osche, *Zoologische Jahrbücher Systems*, 82:618 (1954).
Parvathi, *Brazilian Journal of Microbiology*, 40: 269 (2009).
Potekhina, *Biochemistry*, 76: 745 (2011).
Priest, in: Sonenshein A L, Hoch J A, Losick R, eds. *Bacillus subtilis* and Other Gram-positive Bacteria: Biochemistry, Physiology, and Molecular Genetics. Washington, D.C.: ASM Press. pp. 3-16 (1993).
Rae, *Pest Management Science*, 63:1153 (2007).
Rae, Journal of Invertebrate Pathology, 104: 222 (2010).
Rashid, *Nematologica*, 34:125 (1988).
Ross, *Molecular Phylogenetics and Evolution*, 55:738 (2010).
Ross, *Journal of Helminthology*, 86:215 (2012).
Satomi, *International Journal of Systematic and Evolutionary Microbiology*, 56: 1735-1740 (2006).
Schneider, *Zeitschrift für wissenschaftliche Zoologie*, 10:176 (1859).
Seibel, *BMC Bioinformatics*, 7:498 (2006).
Seinhorst, *Nematologica*, 4:67 (1959).
Tandingan De Ley, *Nematology*, 16:1129 (2014).
Tandingan De Ley, *Nematology*, 16:175 (2016).
Tavare, Some probabilistic and statistical problems on the analysis of DNA sequences. Lecture Notes on Mathematical Modelling in the Life Sciences 17, 262-272 (1986).
Tirumalai *PLoS ONE* 8 (6). doi:10.1371/journal.pone.0066012.
Van Megen, *Nematology*, 11:927 (2009).
Wang, *Eur J Clin Microbiol Infect Dis* 31, 389 (2012).
Ware, *Journal of Comparative Neurology*, 162:71 (1975).
Williams, *Journal of Invertebrate Pathology*, 127, 122 (2015).
Wilson, *Biocontrol Science and Technology*, 3: 513 (1993).
Wilson, *New Zealand Plant Protection*, 65:161 (2012).
Wilson, in: Campos-Herrera, R. ed. Nematode Pathogenesis of Insects and other Pests. Ecology and Applied Technologies for Sustainable Plant and Crop Protection. Switzerland: Springer Intl. Publishing. pp. 509-521 (2015).
Wuyts, *Nucleic Acids Research*, 32:D101 (2004).
Zaborski, *Journal of Invertebrate Pathology*, 77:282 (2001).

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for inhibiting or treating a mollusk infestation in soil comprising applying to the soil an effective amount of a composition comprising one or more isolated *Phasmarhabditis* nematodes that have been cultured with a nematode growth promoting bacterium, and a suitable carrier or encapsulation agent, wherein at least one of the isolated nematodes is *Phasmarhabditis californica*, and wherein the growth-promoting bacterium comprises *Alcaligenes faecalis*, *Bacillus safensis*, or *Ochrobactrum* sp.

2. The method of claim 1 wherein the mollusk is *C. aspersum*, *D. reticulatum*, *L. flavus*, *L. valentiana* or *L. fulica*.

3. The method of claim 1 wherein the composition is applied before soil cultivating, preplant, or during planting.

4. The method of claim 1 wherein the composition further includes *P. hermaphrodita*, *P. neopapillosa* or *P. papillosa*.

5. The method of claim 1 wherein therein the growth-promoting bacterium comprises *Alcaligenes faecalis*, or *Ochrobactrum* sp.

6. The method of claim 1 wherein the carrier comprises clay.

7. The method of claim 1 wherein the composition is in the form of a water-dispersable powder.

8. The method of claim 1 wherein the carrier is calcium montmorillonite clay, and the nematode concentration is from about $0.1 \times 10^6$ to about $2.0 \times 10^6$ per gram of total composition (wet weight).

9. The method of claim 8 wherein the nematode concentration is from about $0.3 \times 10^6$ to about $1.6 \times 10^6$ per gram of the total composition (wet weight).

10. The method of claim 1 wherein the composition further comprises *P. hermaphrodita* but does not comprise *Moraxella osloensis*.

11. The method of claim 1 wherein the effective amount treat the infestation.

* * * * *

UNITED STATES PATENT AND TRADEMARK OFFICE
CERTIFICATE OF CORRECTION

| | | |
|---|---|---|
| PATENT NO. | : 10,772,333 B2 | |
| APPLICATION NO. | : 15/765456 | |
| DATED | : September 15, 2020 | |
| INVENTOR(S) | : De Ley et al. | |

It is certified that error appears in the above-identified patent and that said Letters Patent is hereby corrected as shown below:

In the Specification

In Column 1, Line 12, after "entirety.", insert --¶GOVERNMENT SUPPORT
This invention was made with government support under 12-25-B-1448 awarded by the United States Department of Agriculture. The government has certain rights in the invention.--

Signed and Sealed this
Thirtieth Day of April, 2024

Katherine Kelly Vidal
*Director of the United States Patent and Trademark Office*